United States Patent [19]
Allet et al.

[11] Patent Number: 5,182,196
[45] Date of Patent: Jan. 26, 1993

[54] EXPRESSION SYSTEMS FOR OVERPRODUCTION OF DESIRED PROTEINS

[75] Inventors: Bernard Allet, Onex; Eric H. Kawashima, Geneva, both of Switzerland

[73] Assignee: Biogen, Inc., Cambridge, Mass.

[21] Appl. No.: 372,281

[22] Filed: Jun. 27, 1989

Related U.S. Application Data

[63] Continuation of Ser. No. 53,398, May 18, 1987, abandoned, which is a continuation-in-part of Ser. No. 785,847, Oct. 9, 1985, abandoned.

[51] Int. Cl.$^5$ .................. C12P 21/02; C12N 15/70; C12N 1/21
[52] U.S. Cl. .................. 435/69.5; 536/23.51; 536/23.5; 435/252.3
[58] Field of Search .................. 435/69.1, 70, 91, 253, 435/172.3; 536/27

[56] References Cited

FOREIGN PATENT DOCUMENTS 041767 12/1981 European Pat. Off. .
118977 9/1984 European Pat. Off. .

OTHER PUBLICATIONS

Kindler et al., Proc. Natl. Acad. Sci., USA vol. 83, pp. 1001-1005, (1986).
Krisch et al., "Nucleotide Sequences Involved in Bacteriophage T4 Gene 32 Translational Self-regulation," *Proc. Natl. Acad. Sci. USA*, 79, 4937-41 (1982).
Fransen et al., "Molecular Cloning of Mouse Tumour Necrosis Factor cDNA and Its Eukaryotic Expression," *Nucleic Acids Research*, 13, 4417-29 (1985).
Remaut et al., "Plasmid Vectors For High-Efficiency Expression Controlled by the $p_L$ Promoter of Coliphage Lambda", *Gene*, 15, 81-93 (1981).
Kindler et al., "Stimulation of Hematopoiesis In Vivo By Recombinant Bacterial Murine Interleukin 3," *Proc. Natl. Acad. Sci. USA*, 83, 1001-05 (1986).
Shirai et al., "Cloning And Expression In *Escherichia coli* Of The Gene For Human Tumour Necrosis Factor," *Nature*, 313, 803-06 (1985).
Lemaire et al., "Autogenous Translational Repression Of Bacteriophage T4 Gene 32 Expression In Vitro," *J. Mol. Biol.*, 126, 73-90 (1978).
Krisch et al., "Stimulation Of The Synthesis Of Bacteriophage T4 Gene 32 Protein By Ultraviolet Light Irradiation," *J. Mol. Biol.*, 108, 67-81 (1976).
Wong et al., "Identification Of A Positive Retroregulator That Stabilizes mRNAs In Bacteria," *Proc. Natl. Acad. Sci. USA*, 83, 3233-37 (1986).
Krisch et al., "Regulation of the Synthesis of Bacteriophage T4 Gene 32 Protein," *J. Mol Biol.*, 88, 89-104 (1974).
Hirashima et al., "Differential Inhibitory Effects of Antiobiotics On The Biosynthesis Of Envelope Proteins of *Escherichia coli*," *J. Mol. Biol.*, 79, 373-89 (1973).
Wang et al., "Molecular Cloning of the Complementary DNA for Human Tumor Necrosis Factor," *Science*, 228, 149-54 (1985).
Bachmann, "Pedigrees Of Some Mutant Strains Of *Escherichia coli* K-12", *Bacter. Rev.*, 36, 525-57 (1972).
Marmenout et al., "Molecular Cloning And Expression Of Human Tumor Necrosis Factor And Comparison With Mouse Tumor Necrosis Factor," *Eur. J. Biochem.*, 152 515-522 (1985).
Pennica et al., "Human Tumour Necrosis Factor: Precursor Structure, Expression And Homology To Lymphotoxin," *Nature*, 312, 724-29 (1984).
Twigg et al., "Trans-complementable Copy-number Mutants Of Plasmid ColE1," *Nature*, 283, 216-18 (1980).
Maxam et al., "A New Method For Sequencing DNA," *Proc. Natl. Acad. Sci. USA*, 74, 560-64.
Laemmli et al., "Cleavage of Structural Proteins During The Assembly Of The Head Of Bacteriophage T4," *Nature*, 227, 680-85.
Oostra et al., "Transforming Activity Of Polyoma Virus Middle-T Antigen Probed By Site-Directed Mutagenesis," *Nature*, 304-456-59.
Bernard et al., "Construction Of Plasmid Cloning Vehicles That Promote Gene Expression From the Bacteriophage Lambda $p_L$ Promoter," *Gene*, 5, 59-76 (1979).
Gorski et al., "The Stability of Bacteriophage T4 Gene 32 mRNA: A 5' Leader Sequence that can Stabilize mRNA Transcripts," *Cell*, 43, 461-69 (1985).

K. Gorski et al., "The Nucleotide Sequences Involved In Bacteriophage T4 Gene 32 mRNA Stability", *Experientia*, 41, p. 801 (1985)(Abstract).

Krisch et al., "Construction and Properties of a Recombinant Plasmid Containing Gene 32 of Bacteriophage T4D", *J. Mol. Biol.*, 148, pp. 199-218 (1981).

N. J. Casna et al., "Bacteriophage T4 As A Generalized DNA-Cloning Vehicle", *Gene*, 18, pp. 297-307 (1982).

P. W. Gray et al., "Cloning and Expression of cDNA For Human Lymphotoxin, A Lymphokine With Tumor Necrosis Activity", *Nature*, 312, pp. 721-24 (1984).

*Primary Examiner*—Richard A. Schwartz
*Assistant Examiner*—S. L. Nolan
*Attorney, Agent, or Firm*—James F. Haley, Jr.; John J. Cassingham; Leon R. Yankwich

[57] ABSTRACT

Recombinant DNA molecules comprising DNA sequences derived from bacteriophage T4 that are useful in expressing desired polypeptides in unexpectedly high yields, hosts and expression systems comprising such recombinant DNA molecules and methods for expressing desired polypeptides in high yields by the utilization of such hosts and expression systems.

13 Claims, 16 Drawing Sheets

FIG.1A
A. PL-T4 VECTOR
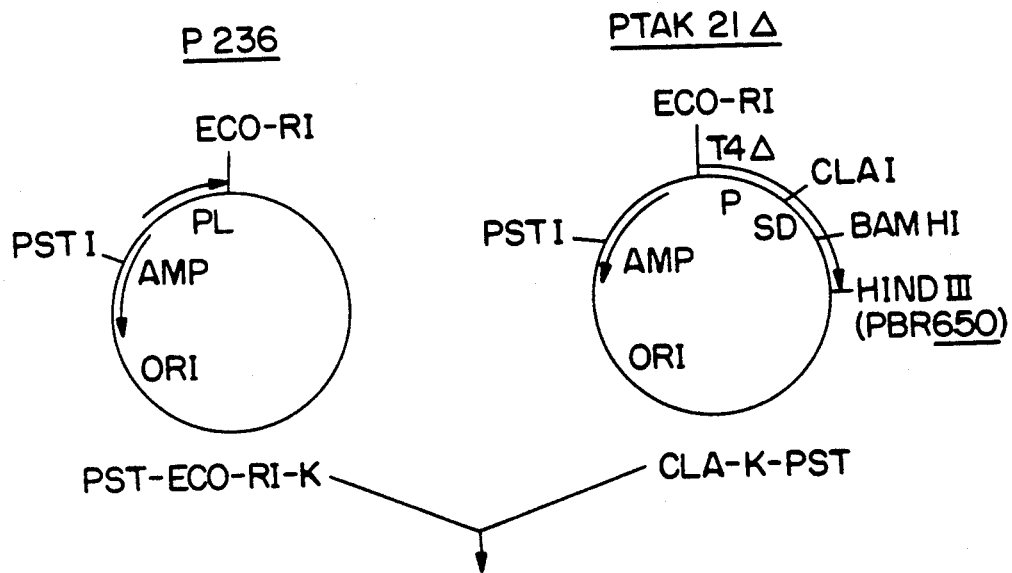
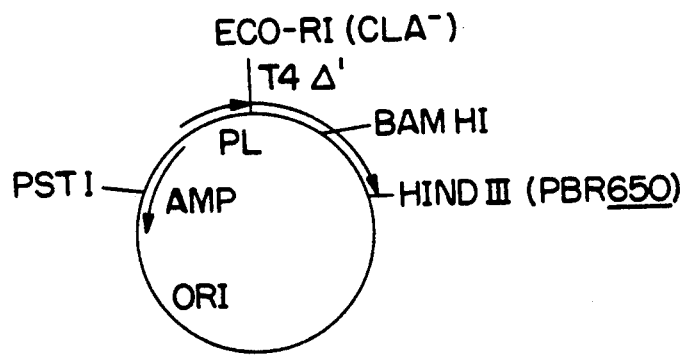
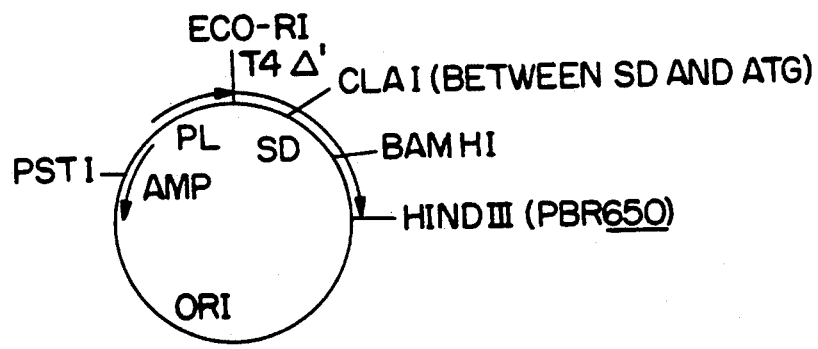

FIG. 1B
B. HTNF (GN) CONSTRUCTION
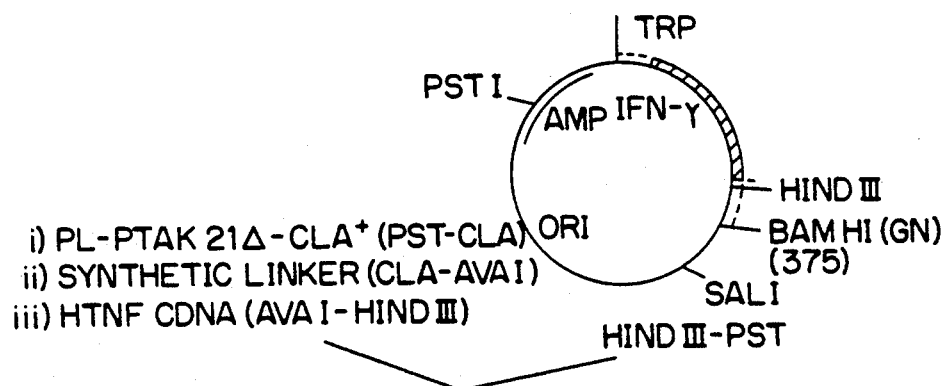
i) PL-PTAK 21Δ-CLA⁺ (PST-CLA)
ii) SYNTHETIC LINKER (CLA-AVA I)
iii) HTNF cDNA (AVA I - HIND III)
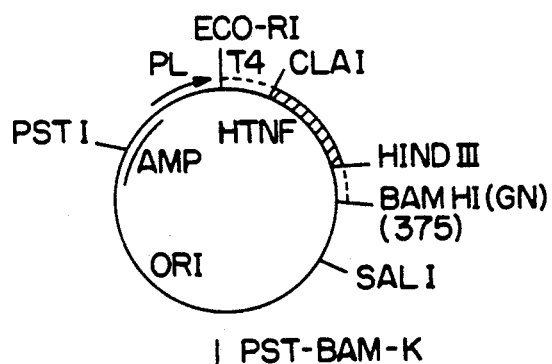
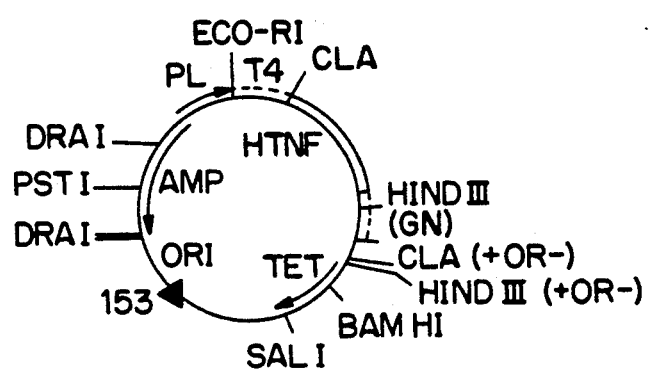

FIG. 1C
C. T4 TER AND Δ PL DERIVATIVES
i) PAT153-PLT4 HTNF-(GN)-SAL
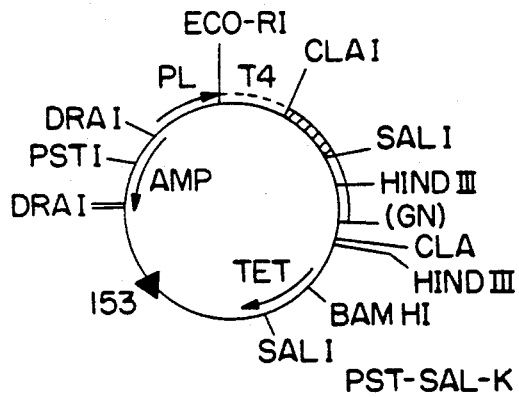
ii) SYNTHETIC T4 TERMINATOR (HIND III-K-ECO-RI)
iii) PAT153 (ECO-RI-PST I)
PAT153-PLT4 HTNF-T4-TER
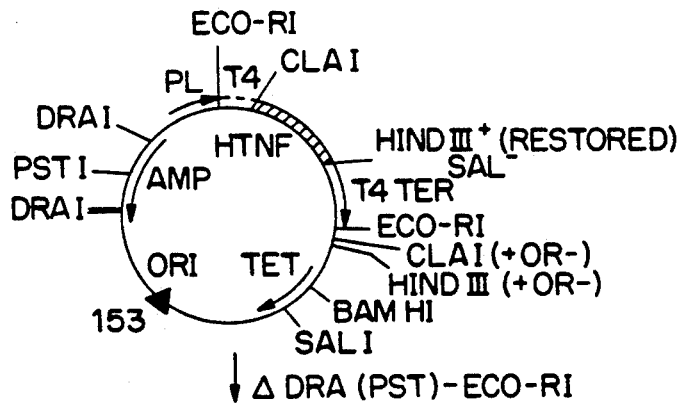
PAT153 T4 HTNF (T4 TER OR GN)
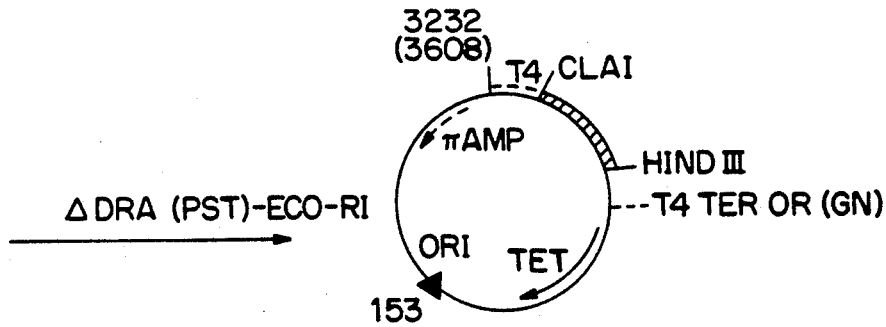

```
                          30                  50
       ----------T4 SEQUENCE I---------------------------
     AATTCATGGTAAAGTATTTCAACTCAGGTTGGATACCTCTCGAAGACCCAGAGTATTGC      60
     TTAAGTACCATTTCATAAAGTTGAGTCCAACCTATGGAGAGCTTCTGGGTCTCATAACG 70           90                 110
     ----------------------------------------------------------------
 61  GAATTATGCCAGCTATGAGGTAAAGTGTCATAGCACCAACTGTTAATTAAATTAAATTAA    120
     CTTAATACGGTCGATACTCCATTTCACAGTATCGTGGTTGACAATTAATTTAATTTAATT 130               150              170
     -------><----syn. linker"CA5"-------------->
121  AAAGGAAATCGATACTAAAATGGTCAGATCATCTTCTCGAACCCCGAGTGACAAGCCTGT    180
     TTTCCTTTAGCTATGATTTTACCAGTCTAGTAGAAGAGCTTGGGGCTCACTGTTCGGACA
                         MetValArgSerSerSerArgThrProSerAspLysProVa
                     <---------------TNF PROTEIN--------

190              210              230
181  AGCCCATGTTGTAGCAAACCCTCAAGCTGAGGGGCAGCTCCAGTGGCTGAACCGCCGGGC    240
     TCGGGTACAACATCGTTTGGGAGTTCGACTCCCCGTCGAGGTCACCGACTTGGCGGCCCG
     lAlaHisValValAlaAsnProGlnAlaGluGlyGlnLeuGlnTrpLeuAsnArgArgAl 250              270              290
241  CAATGCCCTCCTGGCCAATGGCGTGGAGCTGAGAGATAACCAGCTGGTGGTGCCATCAGA    300
     GTTACGGGAGGACCGGTTACCGCACCTCGACTCTCTATTGGTCGACCACCACGGTAGTCT
     aAsnAlaLeuLeuAlaAsnGlyValGluLeuArgAspAsnGlnLeuValValProSerGl 310              330              350
301  GGGCCTGTACCTCATCTACTCCCAGGTCCTCTTCAAGGGCCAAGGCTGCCCCTCCACCCA    360
     CCCGGACATGGAGTAGATGAGGGTCCAGGAGAAGTTCCCGGTTCCGACGGGGAGGTGGGT
     uGlyLeuTyrLeuIleTyrSerGlnValLeuPheLysGlyGlnGlyCysProSerThrHi 370              390              410
361  TGTGCTCCTCACCCACACCATCAGCCGCATCGCCGTCTCCTACCAGACCAAGGTCAACCT    420
     ACACGAGGAGTGGGTGTGGTAGTCGGCGTAGCGGCAGAGGATGGTCTGGTTCCAGTTGGA
     sValLeuLeuThrHisThrIleSerArgIleAlaValSerTyrGlnThrLysValAsnLe 430              450              470
421  CCTCTCTGCCATCAAGAGCCCCTGCCAGAGGGAGACCCCAGAGGGGGCTGAGGCCAAGCC    480
     GGAGAGACGGTAGTTCTCGGGGACGGTCTCCCTCTGGGGTCTCCCCCGACTCCGGTTCGG
     uLeuSerAlaIleLysSerProCysGlnArgGluThrProGluGlyAlaGluAlaLysPr 490              510              530
481  CTGGTATGAGCCCATCTATCTGGGAGGGGTCTTCCAGCTGGAGAAGGGTGACCGACTCAG    540
     GACCATACTCGGGTAGATAGACCCTCCCCAGAAGGTCGACCTCTTCCCACTGGCTGAGTC
     oTrpTyrGluProIleTyrLeuGlyGlyValPheGlnLeuGluLysGlyAspArgLeuSe 550              570              590
541  CGCTGAGATCAATCGGCCCGACTATCTCGACTTTGCCGAGTCTGGGCAGGTCTACTTTGG    600
     GCGACTCTAGTTAGCCGGGCTGATAGAGCTGAAACGGCTCAGACCCGTCCAGATGAAACC
     rAlaGluIleAsnArgProAspTyrLeuAspPheAlaGluSerGlyGlnValTyrPheGl
```

FIG. 3A

```
                610               630                650
                         <------syn. T4 gene 32 terminator-->
601     GATCATTGCCCTGTGAGTCGAAGCTTGGGGACCCTAGAGGTCCCCTTTTTTATTTTGAAT    660
        CTAGTAACGGGACACTCAGCTTCGAACCCCTGGGATCTCCAGGGGAAAAAATAAAACTTA
        yIleIleAlaLeuEnd

```
                    10                  30                  50
         <------------------pL promoter---------------------
    1    CTGCAGCCCACGATGCGTCCGGCGTAGAGGATCTCTCACCTACCAAACAATGCCCCCCTG    60
         GACGTCGGGTGCTACGCAGGCCGCATCTCCTAGAGAGTGGATGGTTTGTTACGGGGGGAC 70                  90                 110
         ------------------------------------------------------------
   61    CAAAAAATAAATTCATATAAAAAACATACAGATAACCATCTGCGGTGATAAATTATCTCT   120
         GTTTTTTATTTAAGTATATTTTTTGTATGTCTATTGGTAGACGCCACTATTTAATAGAGA 130                 150                 170
         ------------------------------------------------------------
  121    GGCGGTGTTGACATAAATACCACTGGCGGTGATACTGAGCACATCAGCAGGACGCACTGA   180
         CCGCCACAACTGTATTTATGGTGACCGCCACTATGACTCGTGTAGTCGTCCTGCGTGACT 190                 210                 230
         ------------------------------------------------------------
  181    CCACCATGAAGGTGACGCTCTTAAAATTAAGCCCTGAAGAAGGGCAGCATTCAAAGCAGA   240
         GGTGGTACTTCCACTGCGAGAATTTTAATTCGGGACTTCTTCCCGTCGTAAGTTTCGTCT 250                 270                 290
         -----------------------------------> <-----T4 sequence---
  241    AGGCTTTGGGGTGTGTGATACGAAACGAAGCATTGGAATTCGATGGTAAAGTATTTCAAC   300
         TCCGAAACCCCACACACTATGCTTTGCTTCGTAACCTTAAGCTACCATTTCATAAAGTTG 310                 330                 350
         ------------------------------------------------------------
  301    TCAGGTTGGATACCTCTCGAAGACCCAGAGTATTGCGAATTATGCCAGCTATGAGGTAAA   360
         AGTCCAACCTATGGAGAGCTTCTGGGTCTCATAACGCTTAATACGGTCGATACTCCATTT 370                 390                 410
         ------------------------------------------------><---syn. linker
  361    GTGTCATAGCACCAACTGTTAATTAAATTAAATTAAAAAGGAAATCGATACTATGGTCAG   420
         CACAGTATCGTGGTTGACAATTAATTTAATTTAATTTTTCCTTTAGCTATGATACCAGTC
                                                          MetValAr
                                                          <-------
                   430                 450                 470
         "CA3"----------->
  421    GTCTTCCTCTCGAACCCCGAGTGACAAGCCTGTAGCCCATGTTGTAGCAAACCCTCAAGC   480
         CAGAAGGAGAGCTTGGGGCTCACTGTTCGGACATCGGGTACAACATCGTTTGGGAGTTCG
         gSerSerSerArgThrProSerAspLysProValAlaHisValValAlaAsnProGlnAl
         ----TNF protein------
                   490                 510                 530
  481    TGAGGGGCAGCTCCAGTGGCTGAACCGCCGGGCCAATGCCCTCCTGGCCAATGGCGTGGA   540
         ACTCCCCGTCGAGGTCACCGACTTGGCGGCCCGGTTACGGGAGGACCGGTTACCGCACCT
         aGluGlyGlnLeuGlnTrpLeuAsnArgArgAlaAsnAlaLeuLeuAlaAsnGlyValGl 550                 570                 590
  541    GCTGAGAGATAACCAGCTGGTGGTGCCATCAGAGGGCCTGTACCTCATCTACTCCCAGGT   600
         CGACTCTCTATTGGTCGACCACCACGGTAGTCTCCCGGACATGGAGTAGATGAGGGTCCA
         uLeuArgAspAsnGlnLeuValValProSerGluGlyLeuTyrLeuIleTyrSerGlnVa
```

FIG. 4A

```
            610                 630                 650
601  CCTCTTCAAGGGCCAAGGCTGCCCCTCCACCCATGTGCTCCTCACCCACACCATCAGCCG      660
     GGAGAAGTTCCCGGTTCCGACGGGGAGGTGGGTACACGAGGAGTGGGTGTGGTAGTCGGC
     lLeuPheLysGlyGlnGlyCysProSerThrHisValLeuLeuThrHisThrIleSerAr 670                 690                 710
661  CATCGCCGTCTCCTACCAGACCAAGGTCAACCTCCTCTCTGCCATCAAGAGCCCCTGCCA      720
     GTAGCGGCAGAGGATGGTCTGGTTCCAGTTGGAGGAGAGACGGTAGTTCTCGGGGACGGT
     gIleAlaValSerTyrGlnThrLysValAsnLeuLeuSerAlaIleLysSerProCysGl 730                 750                 770
721  GAGGGAGACCCCAGAGGGGGCTGAGGCCAAGCCCTGGTATGAGCCCATCTATCTGGGAGG      780
     CTCCCTCTGGGGTCTCCCCCGACTCCGGTTCGGGACCATACTCGGGTAGATAGACCCTCC
     nArgGluThrProGluGlyAlaGluAlaLysProTrpTyrGluProIleTyrLeuGlyGl 790                 810                 830
781  GGTCTTCCAGCTGGAGAAGGGTGACCGACTCAGCGCTGAGATCAATCGGCCCGACTATCT      840
     CCAGAAGGTCGACCTCTTCCCACTGGCTGAGTCGCGACTCTAGTTAGCCGGGCTGATAGA
     yValPheGlnLeuGluLysGlyAspArgLeuSerAlaGluIleAsnArgProAspTyrLe 850                 870                 890
                                                    <-----
841  CGACTTTGCCGAGTCTGGGCAGGTCTACTTTGGGATCATTGCCCTGTGAGTCGAAGCTTG      900
     GCTGAAACGGCTCAGACCCGTCCAGATGAAACCCTAGTAACGGGACACTCAGCTTCGAAC
     uAspPheAlaGluSerGlyGlnValTyrPheGlyIleIleAlaLeuEnd 910         930
     --syn. T4 terminator--------->
901  GGGACCCTAGAGGTCCCCTTTTTTATTTTGAATTC  935
     CCCTGGGATCTCCAGGGGAAAAAATAAAACTTAAG
```

FIG. 4B

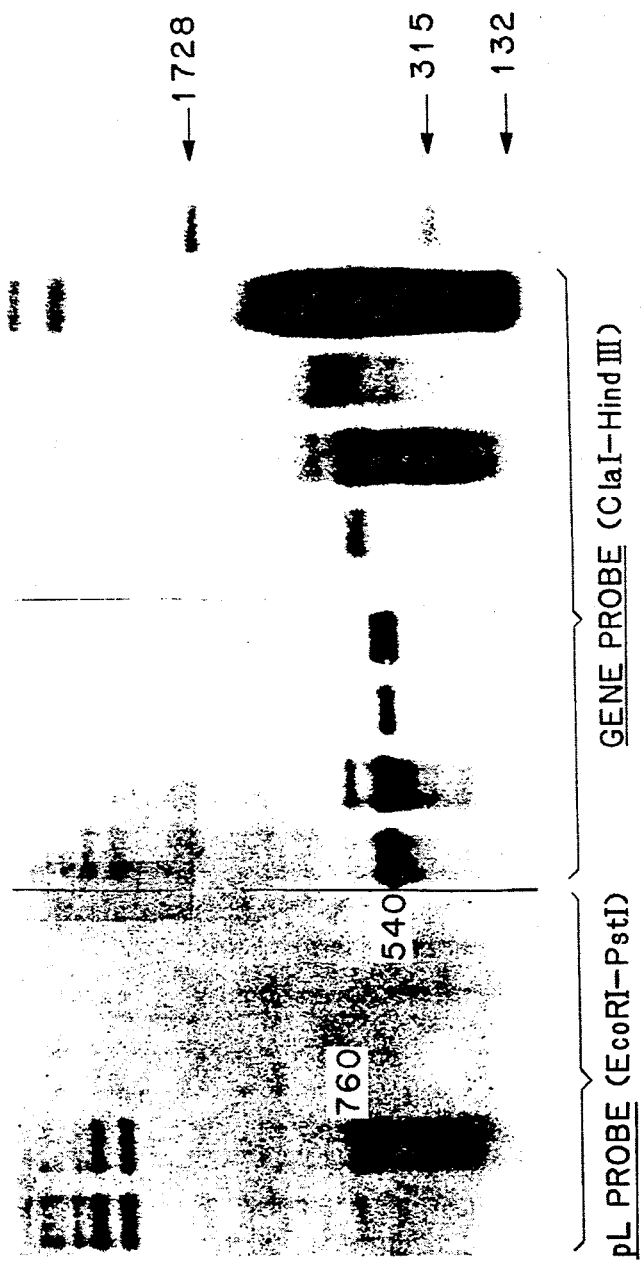

5,182,196

EXPRESSION SYSTEMS FOR OVERPRODUCTION OF DESIRED PROTEINS

This is a continuation of application Ser. No. 53,398, filed May 18, 1987, now abandoned, which is a continuation-in-part of Ser. No. 785,847, filed Oct. 9, 1985, now abandoned.

TECHNICAL FIELD OF THE INVENTION

This invention relates to expression systems for overproduction of desired proteins and to a method for stabilizing mRNA in such expression systems. More particularly, it relates to recombinant DNA molecules comprising DNA sequences derived from bacteriophage T4 that are useful in expressing desired proteins in unexpectedly high yields and to hosts and expression systems comprising such recombinant DNA molecules. This invention also relates to an expression system, characterized by such a DNA sequence, a synthetic oligonucleolide sequence and an appropriate terminator sequence. Such expression systems are useful in expressing desired proteins in unexpectedly high yields and in stabilizing mRNA and thus facilitating the expression of desired proteins in high yields.

BACKGROUND OF THE INVENTION

Recombinant DNA techniques have made it possible to prepare proteins and polypeptides, such as interferons and various hormones, that were heretofore unavailable in significant amounts, by culturing host cells transformed with a DNA sequence coding for those proteins or polypeptides and isolating the produced protein. Although much progress has been made in obtaining significant amounts of proteins relatively inexpensively, there is considerable room for improvement.

The level of production of a protein in a host cell is governed by three major factors: the number of copies of its gene within the cell, the efficiency with which those gene copies are transcribed and the efficiency with which the resultant messenger RNA ("mRNA") is translated. Optimization of each of these factors is desirable if a protein is to be made available at reasonable cost.

An expression system for producing a desired protein usually consists of seven basic elements:

(i) A recombinant DNA molecule (e.g., a plasmid) containing a region necessary for stable replication and copy number control (the replicon region).

(ii) A selectable marker such as a gene conferring antibiotic resistance to the host.

(iii) A promoter for transcription initiation and control.

(iv) A ribosome binding site for translation initiation at the appropriate ATG triplet (trinucleotide) sequence.

(v) DNA sequences compatible with efficient translation of mRNA.

(vi) An appropriate host.

(vii) Appropriate growth conditions.

Each of these elements, both independently and in connection with the others, can affect expression. For example, the properties of the protein to be expressed, such as the size, the number of cysteines, the folding properties and the solubility of the protein in the environment of the host or the media, may have a significant effect on the functioning of an expression system. Even the antibiotic resistance marker, which might be expected to have very little to do with the level of expression of an unrelated gene product, can lead to plasmid instability and ultimately affect expression. Also, since a DNA sequence coding for a desired protein, and the mRNA sequence derived therefrom, will generally code for a large number (e.g., more than 100) of amino acids in sequence, the efficiency of translation of mRNA will have a substantial effect on expression. For the foregoing reasons, it is important to design the construction of the expression system with the best combination of the aforementioned seven elements.

Efficiency of transcription and translation (which together comprise expression) is in part dependent upon the nucleotide sequences which are normally situated ahead (upstream) of the desired coding sequence or gene, those sequences within gene coding sequences and those sequences following (downstream) the desired coding sequences. For example, the upstream nucleotide sequences or expression control sequences define, inter alia, he location at which RNA polymerase interacts (the promoter sequence) to initiate transcription of mRNA and at which ribosomes bind (the ribosome binding site) and interact with the mRNA (the product of transcription) to initiate translation. Sequences of the coding sequence and downstream of it may also modulate the level of expression, presumably because of secondary structures formed in the mRNA.

SUMMARY OF THE INVENTION

We have found that particularly efficient expression of desired proteins may be obtained by utilizing, as part of an expression system, a recombinant DNA molecule comprising a DNA sequence derived from bacteriophage T4.

The aforementioned sequence, which is a deletion derivative of the phage T4 protein 32 (gp 32) gene (see H. M. Krisch and B. Allet, *Proc. Natl. Acad. Sci.*, 79, 4937–41 (1982)) has never been described as an effective promoter of DNA expression. Furthermore, we have also unexpectedly found that mRNA that is translatable to a desired protein is unusually stable in *E.coli* when it initiates in the T4-derived DNA sequence of this invention.

While we do not wish to be bound by any theory, we believe that at least one reason why the DNA sequence utilized in our invention is so effective is that within said DNA sequence there are three or four contiguous segments, each of which may function as a promoter (i.e., to initiate transcription of mRNA) in sequence, and that these several promoters may sequester several RNA polymerase molecules, initiating more mRNAs than would a single promoter.

The present invention relates to a recombinant DNA molecule comprising the DNA sequence

```
CGATGGTAAAGTATTTCAACTCAGGTTGGATACCTCTCGAAGACCCAGAG
TATTGCGAATTATGCCAGCTATGAGGTAAAGTGTCATAGCACCAACTGTTA
ATTAAATTAAATTAAAAAGGAAAT
```

(hereinafter referred to as sequence I).

The present invention also relates to a recombinant DNA molecule comprising a DNA sequence that codes for a desired polypeptide and that is operatively-linked to the downstream end of sequence I. The DNA sequence coding for a desired polypeptide may be a gene. The term "operatively-linked" includes having an appropriate start signal (for example, ATG) in front of the DNA sequence encoding the desired product and maintaining the correct reading frame to permit expression of the DNA sequence under the control of the expression control sequence and production of the desired product encoded for by that DNA sequence, and also includes the possibility of having sequence I linked, through a sequence X (as described below), to the DNA sequence that codes for a desired product. If a gene that one desires to insert into a recombinant DNA molecule does not contain an appropriate start signal, such a start should be inserted in front of the gene.

The present invention also relates to a recombinant DNA molecule comprising a DNA sequence that codes for a desired polypeptide and that is operatively-linked through an oligonucleotide sequence X (wherein X is a group of 1 to 15 bases) to the downstream end of sequence I. One skilled in the art may choose different combinations of bases within the definition of X to optimize expression levels in particular situations or to confer other desirable properties upon the recombinant DNA molecules of the present invention. Preferably, sequence X is selected from the group consisting of CGATACT, CGCGATACT, ATACTAAA, ATACT, CGCGATACTAAA, CGATACTAAA and CGATTCC.

Synthetic oligonucleotide linkers may be used to link sequence I to a DNA sequence coding for a particular polypeptide in a recombinant DNA molecule. The synthetic oligonucleotide linker is synthesized chemically by known means and attached to the downstream end of sequence I. The linker preferably comprises a restriction enzyme site at its upstream end for use in linking it to sequence I. For example, in the embodiments of this invention where sequence I is isolated using ClaI restriction, the linker carries at its upstream end a corresponding ClaI site. Thus, after the synthetic oligonucleotide linker is cut with the restriction enzyme, it may be easily linked to sequence I. The linker also preferably comprises a restriction site at its downstream end so that it can be easily linked to DNA sequences coding for desired polypeptides. In situations where part of the gene necessary to encode the desired polypeptide would be deleted by restriction for combination with the linker, the synthetic oligonucleotide linker may be constructed so as to supply the necessary DNA sequence (including an appropriate start signal). After insertion of sequence I by the use of such a synthetic oligonucleotide linker (i.e., a linker comprising a group of bases within the definition of X and, if necessary, a group of bases to reconstruct the gene that is desired to be expressed, but has been cleaved by the restriction enzyme) the resulting DNA sequence in which the gene is operatively-linked through sequence X to sequence I may be schematically illustrated, for example, as follows: sequence I-X-gene. In the foregoing schematic illustration, it will be understood that the required start signal is present at the downstream end of X or at the upstream end of the gene.

When the gene coding for the desired polypeptide is the human tumor necrosis factor (HTNF) gene, preferred X sequences are CGATACT, CAATAAA and CGATTCC. Polynucleotide sequences comprising sequence I connected to one of these preferred X sequences and a group of bases necessary to reconstruct the HTNF gene and an ATG start signal which has been deleted by cleavage with AvaI may be prepared by attaching one of the following synthetic oligonucleotide linkers to sequence I: CA1, CA-his, CA3, CA5, Δ2 and CA13 (see Table 1). The resulting sequence may then be inserted into a recombinant DNA molecule as described above. The resulting recombinant DNA molecule may then be introduced into an appropriate host, e.g., *E.coli*, to produce the HTNF polypeptide. (For a discussion of human tumor necrosis factor see U.S. patent application Ser. No. 684,595, filed Dec. 21, 1984.)

A preferred embodiment of the present invention relates to a recombinant DNA molecule comprising sequence I and further comprising (a) an oligonucleotide sequence X; (b) a transcription terminator sequence, preferably the T4 gene 32 transcription terminator (hereinafter designated "Ter", see Table 1) or another appropriate terminator sequence (for example, the cry transcription terminator from *Bacillus thuringiensis* vs. *Kurstaki* HD-1 (Wong et al., *Proc. Natl. Acad. Sci. USA*, 83, 3233–37 (1986)) or the $T_J$ transcription terminator from bacteriophage $\phi$X174 (Hayashi et al., *Nucleic Acids Res.*, 13, 5937–48 (1985))); or, (c) both the foregoing sequence X and the foregoing transcription terminator sequence. The construction of such a preferred embodiment of the present invention may be schematically illustrated, for example, as follows: sequence I - X - gene - Ter. In the foregoing schematic illustration, it will be understood that the required start signal is present at the downstream end of X or at the upstream end of the gene. This molecule is useful in the expression in appropriate hosts of DNA sequences coding for desired products.

Thus, the present invention also relates to a host or expression system comprising a recombinant DNA molecule comprising sequence I operatively-linked to a DNA sequence coding for a desired polypeptide, and to the use of such a host or expression system in stabilizing mRNA and expressing a desired protein. Of course, in preferred hosts and expression systems said recombinant DNA molecule will also comprise one of the foregoing X sequences, one of the foregoing transcription terminator sequences or both.

TABLE 1

| Synthetic oligonucleotides |
|---|
| CA1 5'- CGATACT ATG GTA CGT TCT TCC TCT CGT ACC<br>GCTATGA TAC CAT GCA AGA AGG AGA GCA TGG |
| CA-his 5'- CGATACT ATG GTA CAT TCT TCC TCT CGT ACC<br>GCTATGA TAC CAT GTA AGA AGG AGA GCA TGG |
| CA3 5'- CGATACT ATG GTC AGG TCT TCC TCT CGA ACC<br>GCTATGA TAC CAG TCC AGA AGG AGA GCT TGG |
| CA5 5'- CGATACTAAA ATG GTC AGA TCA TCT TCT CGA ACC<br>GCTATGATTT TAC CAG TCT AGT AGA AGA GCT TGG |

TABLE 1-continued

Synthetic oligonucleotides

Δ2 5'- CGAT ACT ATG AGC AGC AGT CGT ACC
GCT ATG A TAC TCG TCG TCT GCA TGG

CA13 5'- CGATTCC ATG GTA CGA AGT AGT AGT CGT ACC
GCT AAGG TAC CAT GCT TCA TCA TCA GCA TGG

Ter 5'- AGCTT GGGGA CCC T AGAGGT CCCC TTTTT TATTTTG
TCGA ACCCC T GGGA TCT CC AGGGG A AAAAAT AAAA CTT AA

BRIEF DESCRIPTION OF THE DRAWINGS

FIG. 1A shows the preparation of plasmid pL-pTAK 21A from the plasmids p236 and pTAK 21Δ. It also shows the preparation of plasmid pL-pTAK 21Δ-Cla+- from pL-pTAK 21Δ. In this figure, and in FIGS. IB and 1C, a K symbol after the site indicates that the site has been treated with the "Klenow" fragment of DNA polymerase I in the presence of the four deoxyribonucleoside triphosphates.

FIG. 1B shows the preparation of plasmid pBR322-pLT4-HTNF-(Gn) from plasmid pBR322-Trp-IFN-γ-(Gn). It also shows the preparation of plasmid pAT153-pLT4-HTNF-(Gn)(Tet)+ from plasmid pBR322-pLT4-HTNF-(Gn).

FIG. 1C shows the preparation of plasmid pAT153-pLT4 HTNF-T4-ter from plasmid pAT153-pLT4 HTNF-(Gn)-Sal; the preparation of plasmid pAT153 T4 HTNF-T4-ter from plasmid pAT153-pLT4 HTNF-T4-ter; and the preparation of plasmid pAT153 T4 HTNF(Gn) from plasmid pAT153-pLT4 HTNF-(Gn)(Tet)+.

FIGS. 3A and FIG. 3B show the DNA and corresponding RNA and amino acid sequences of the plasmid 153-T4 CA5 Dra T4-ter from the Dra I AATTC EcoRI site to the EcoRI site located at the end of the T4-ter HTNF gene.

FIG. 4A and FIG. 4B show the DNA and corresponding RNA and amino acid sequences of the plasmid 153-pL CA3-cts T4-ter from the PstI site to the EcoRI site situated at the 3' end of the T4 terminator.

FIG. 6(a) shows the Northern blot analysis of RNA samples prepared from the indicated strains (all Ter).

FIG. 6(b) shows the indicated samples analyzed as in (a), using the radioactive HTNF gene probe to detect RNA.

FIG. 7B also shows the results of gradient SDS-polyacryamide gel electrophoresis of HTNF protein samples prepared from cells harboring plasmids comprising the Taq-4, Bal4, Ba18 and Bal11 sequences.

DETAILED DESCRIPTION OF THE INVENTION

Figure 2:
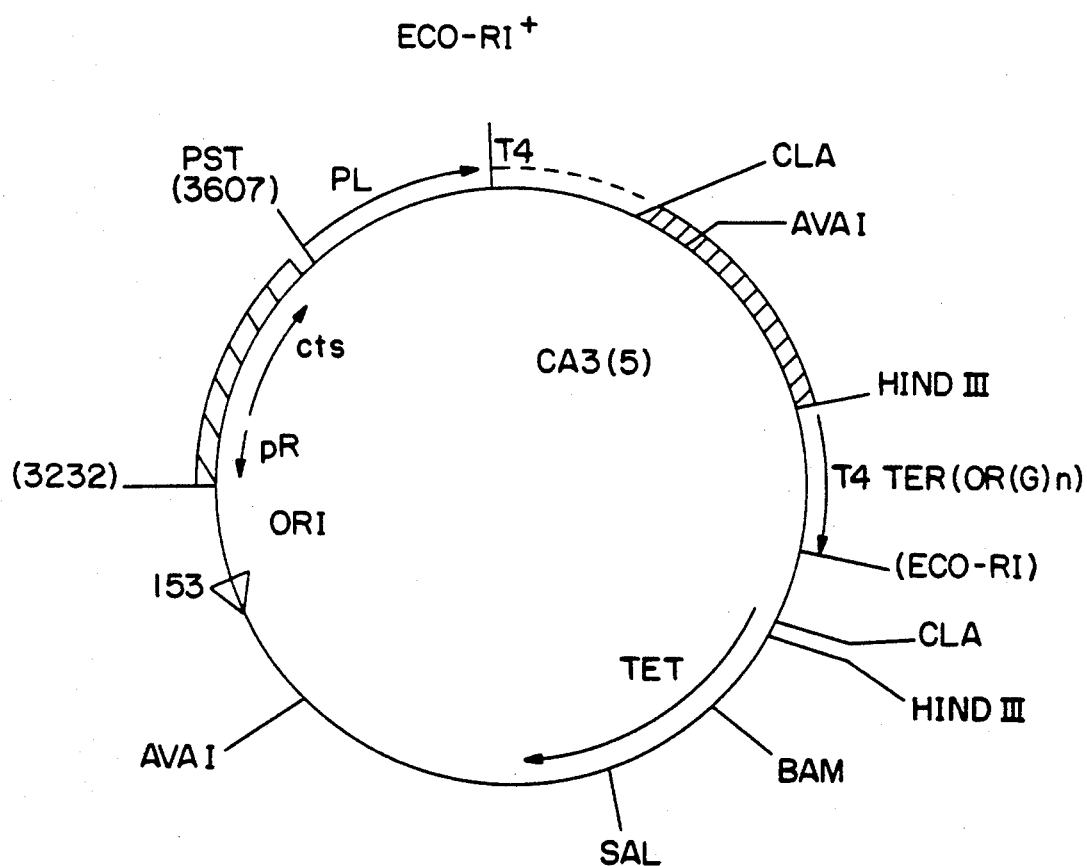
FIG. 2 shows the structure of plasmid pLT4 CA3(5) cts T4-ter.

Sequence I may be chemically synthesized by techniques well-known in the art, for example, by using an automated synthesizer such as the Applied Biosystems 380A automated synthesizer. Alternatively, sequence I may be obtained, as described in Example 1 below, from plasmid pTAK21Δ (FIG. 1A) (see Gorski et al., *Cell*, 43, 461–69 (1985)).

When the use of a synthetic oligonucleotide linker or transcription terminator, e.g., the T4 gene 32 transcription terminator (see Table 1), is desired, the linker or terminator may be synthesized by we-known techniques, e.g., for example, use of the Applied Biosystems 380A automated synthesizer, as described in Examples 2 and 3 below.

It should be understood that the DNA sequences that code for the desired polypeptides that may be produced in high yield using this invention may include nucleotides which are not part of the actual gene coding for the particular polypeptide. For example, the DNA sequences may be fused in the same reading frame to a portion of a DNA sequence coding for at least one eukaryotic or prokaryotic carrier protein or to a DNA sequence coding for at least one eukaryotic or prokaryotic signal sequence, or combinations thereof. Such constructions may aid in expression of the desired DNA sequence, improve purification or permit secretion, and preferably maturation, of a desired polypeptide from the host cell. The DNA sequence may alternatively include an ATG start codon, alone or together with other codons, fused directly to the sequence encoding the first amino acid of a desired polypeptide. Such constructions enable the production of, for example, a methionyl or other peptidyl polypeptide. This N-terminal methionine or peptide may then, if desired, be cleaved intra- or extra-cellularly by a variety of known processes or the polypeptide used together with the methionine or other fusion attached to it in various compositions and methods.

In view of the foregoing, it will be clear to one skilled in the art that unless indicated otherwise a reference to a DNA sequence coding for a desired polypeptide may include DNA sequences such as those described in the preceding paragraph.

One skilled in the art may choose different combinations of bases within the definition of X to optimize expression levels in particular situations or to confer other desirable properties upon the recombinant DNA molecules of the present invention. Sequences that have been prepared as described above within the definition of X as well as other portions of the synthetic oligonucleotide linker sequences may be modified by various methods in order to prepare other sequences for use in the recombinant DNA molecules of the present invention. Such methods include, for example (1) site specific mutagenesis (see B. A. Ooostra et al., Nature, 304, 456-59 (1983)); (2) site manipulation at the ClaI site within sequence X, (e.g., use of a Klenow fragment to fill in nucleotides or a S1/Bal digestion to delete nucleotides); and (3) insertion of synthetic oligonucleotide fragments. We used methods (2) and (3) in preparing the plasmids of the present invention.

Methods for expressing proteins are well known. They include transforming an appropriate host with a DNA sequence, culturing the host under appropriate conditions of growth and collecting the desired polypeptide from the culture. It is most preferred that the host cells be allowed to reach stationary phase before the desired polypeptide is collected. Those of skill in the art may select from known methods those that are most effective for expression of a particular gene without departing from the scope of this invention.

The DNA sequences of the present invention may be used in a wide variety of vectors. These include, for example, vectors consisting of segments of chromosomal, non-chromosomal and synthetic DNA sequences, such as various known derivatives of SV40, known bacterial plasmids, e.g., plasmids from E.coli including col E1, pCR1, pBR322, pMB9 and their derivatives, wider host range plasmids, e.g., RP4, phage DNAs, e.g., the numerous derivatives of phage λ, e.g., NM 989, and other DNA phages, e.g., M13 and filamentous single stranded DNA phages, and vectors derived from combinations of plasmids and phage DNAs, such as plasmids which have been modified to employ phage DNA or other expression control sequences. The preferred vectors are pBR322 derivatives.

Within each specific cloning or expression vehicle, various sites may be selected for insertion of the DNA sequences of this invention. These sites are usually designated by the restriction endonuclease which cuts them and are well recognized by those of skill in the art. Various methods for inserting DNA sequences into these sites to form recombinant DNA molecules are also well known. These include, for example, dG-dC or dA-dT tailing, direct ligation, synthetic linkers, exonuclease and polymerase-linked repair reactions followed by ligation, or extension of the DNA strand with DNA polymerase and an appropriate single-stranded template followed by ligation. It is, of course, to be understood that a cloning or expression vehicle useful in this invention need not have a restriction endonuclease site for insertion of the chosen DNA fragment. Instead, the vehicle could be joined to the fragment by alternative means.

The vector or expression vehicle, and, in particular, the sites chosen therein for insertion of the selected DNA fragment and the expression control sequences employed in this invention are determined by a variety of factors, e.g., number of sites susceptible to a particular restriction enzyme, size of the protein to be expressed, expression characteristics such as the location of start and stop codons relative to the vector sequences, and other factors recognized by those of skill in the art. The choice of a vector, expression control sequence, and insertion site for a desired protein sequence is determined by a balance of these factors, not all selections being equally effective for a given case.

In a preferred embodiment of this invention, a synthetic oligonucleotide linker is used to accomplish insertion of the sequence I into a DNA molecule comprising a DNA sequence coding for a particular polypeptide. We have found that plasmids constructed with the linkers CA-his, CA5 or Δ2 (Table 1) express very high levels of HTNF protein. While not wishing to be bound by any theory, we believe that the choice of an appropriate synthetic oligonucleotide linker most probably affects translation efficiency by increasing or decreasing the frequency of base pairing of homologous sequences on the mRNA.

Although the DNA sequences of the present invention comprise a promoter, an additional promoter may be added to such DNA sequences, preferably upstream of such DNA sequences. Such useful promoters include, for example, T4 promoters, the early and late promoters of SV40, the lac system, the trp system, the TAC or TRC system, the major promoter regions of phage λ, the control regions of fd coat protein, the promoter for 3-phosphoglycerate kinase or other glycolytic enzymes, the promoters of acid phosphatase, e.g., Pho5, the promoters of the yeast α-mating factors, and other sequences known to control the expression of genes of prokaryotic or eukaryotic cells or their viruses, and various combinations thereof. In mammalian cells, it is additionally possible to amplify the expression units by linking the gene to that coding for dehydrofolate reductase and applying a selection to host Chinese hamster ovary cells.

In one embodiment of the present invention, the sequence I is inserted downstream of a $P_L$ promoter (see H. Bernard et al., Gene, 5, 59-76 (1979), and European Patent Application Number 81.301413.1, Publication Number 0041767).

We prefer not to make use of the $P_L$ promoter unless it is advantageous to do so because use of the $P_L$ promoter may limit the range of usable hosts to those with λ repressors. However, using the aforementioned DNA sequence I downstream of a $P_L$ promoter is generally advantageous because it may result, in some cases, in higher expression. For example, we have found this to be the case in the expression of murine interleukin 3 (see V. Kindler et al., Proc. Natl. Acad. Sci. USA, 83, 1001-05 (1986)), human interleukin 2 (see European Patent Application Number 84300439.1, Publication Number 0118977), and murine tumor necrosis factor (Fransen et al., Nucleic Acid Res., 13, 4417-30 (1985)).

However, in some cases, use of the aforementioned DNA sequence without a $P_L$ promoter achieves expression levels that are comparable to or higher than those achieved with the combination of said DNA sequence and the $P_L$ promoter. In such cases, the $P_L$ promoter may be dispensed with. We have found this to be the case in the expression of HTNF wherein the expression system is characterized by the T4 gene 32 transcription terminator and sequence I when sequence I is inserted into the recombinant DNA molecule by the use of a preferred synthetic oligonucleotide linker of the present invention.

In a preferred embodiment of this invention, sequence I is used in combination with the T4 gene 32 transcription terminator (see Table 1). The Ter sequence is positioned at the downstream end of the gene which codes for the desired polypeptide and said gene is operatively-linked at its upstream end to sequence I. The terminator is a DNA signal which operates to halt synthesis of mRNA, initiated at the T4 promoters, at a specific site on the DNA template, thus resulting in the production of mRNA molecules (transcription units) of discrete sizes. When this combination is used, the mRNA initiated at the T4 promoter is unusually stable and very high amounts of eukaryotic proteins are synthesized.

Other transcription terminator sequences may be used to increase the stability of mRNAs in the method of the present invention. Increased mRNA stability is generally achieved by mechanisms involving mRNA secondary structures. For example, it has been shown that the cry transcription terminator sequence of Bacillus thuringiensis vs. Kurstaki HD-1 contains an inverted repeat signal and that transcription of this sequence may result in the incorporation of a corresponding stem-and-loop (hairpin) structure at the 3' end of the mRNA. This structure thus apparently protects the mRNAs from exonucleolytic degradation from the 3' end and thereby increases the mRNA half-life (Wong et al., Proc. Natl. Acad. Sci. USA, 83, 3233-37 (1986)). On the other hand, the $T_J$ terminator of bacteriophage $\phi X174$ may enhance mRNA stability by a mechanism in which a stem-and-loop secondary structure is not the primary requirement for the enhancing activity (see Hayashi et al., Nucleic Acids Res., 13, 5937-48 (1985)). While we do not wish to be bound by any theory, we believe that the T4 gene 32 transcription terminator sequence of the present invention allows the formation of a hairpin structure on the mRNA and that this hairpin has the effect of impairing post-transcriptional 3' to 5' exonucleolytic mRNA degradation, thereby enhancing mRNA stability and the level of protein synthesis of the target gene.

In a more preferred embodiment of the present invention, a synthetic oligonucleotide linker selected from the group consisting of CA-his, CA5 and Δ2 (see Table 1) is used to accomplish insertion of sequence I into a DNA molecule comprising a DNA sequence which codes for the HTNF polypeptide and which is fused at its downstream end to a sequence comprising the T4 gene 32 transcription terminator.

A recombinant DNA molecule containing the desired gene operatively-linked to an expression control sequence may be employed to transform a wide variety of appropriate hosts so as to permit such hosts (transformants) to express the gene, or fragment thereof, and to produce the polypeptide, or portion thereof, for which the hybrid DNA codes. The recombinant DNA molecule may also be employed to transform a host so as to permit that host, on replication, to produce additional recombinant DNA molecules as a source of desired genes and fragments thereof.

A wide variety of hosts are also useful in the method of this invention. These hosts include, for example, bacteria, such as E.coli (for example, E.coli HB101 or E.coli MC1061), Bacillus, Streptomyces, and Pseudomonas, fungi, such as yeasts, and animal cells, such as CHO cells, mouse, swine, bovine, fowl or fish cells, plant cells in tissue culture, human tissue cells, or other hosts known in the art. The host selected for a particular application, however, should be one in which the promoter that is contained within the DNA sequences of the present invention is operative.

The selection of an appropriate host for use in the method of this invention is controlled by a number of factors recognized by the art. These include, for example, compatibility with the chosen vector, toxicity of the co-products, ease of recovery of the desired polypeptide, expression characteristics, biosafety and costs. No absolute choice of host may be made for a particular recombinant DNA molecule or polypeptide from any of these factors alone. Instead, a balance of these factors must be struck with the realization that not all hosts may be equally effective for expression of a particular recombinant DNA molecule. In a preferred embodiment of this invention, we employed E.coli W3110 and the plasmids pLT4-CA3 cts T4-ter and T4-CA5 T4-ter. E.coli W3110, 153 pLT4-CA3 cts T4-ter, a preferred E.coli, was deposited with the Deutsche Sammlung von Microorganismen (DSM) on Aug. 29, 1985 under accession number DSM 3460. A second preferred E.coli, E.coli W3110, 153 T4-CA5 T4-ter, was deposited with the DSM on Aug. 29, 1985 under accession number DSM 3461.

Among the polypeptides that have been prepared using the DNA sequences of the present invention are human intereukin 2 and human tumor necrosis factor. Other desired polypeptides may similarly be prepared.

In order that this invention may be better understood, the following examples, for illustrative purposes only, are described. All temperatures referred to in the Examples are in degrees Celsius.

EXAMPLE 1

Preparation of Plasmid $P_L$-PTAK 21 Δ'-CLA+

In order to prepare plasmid pL-pTAK 21 Δ'-Cla+, we first opened the plasmid p236 (see FIG. 1A, European Patent Application Number 81.301413.1, Publication Number 0041767, and E. Remaut et al., Gene, 15, 81-93 (1981)) with restriction endonuclease EcoR1. We filled in the site with DNA polymerase in the presence of both dATP and dTTP, then cleaved with restriction endonuolease PstI. We isolated the smaller resulting fragment which had a size of about 1150 base pairs and contained the $P_L$ sequence.

In parallel, we took a second plasmid pTAK 21Δ (FIG. 1A) (see Gorski et al., Cell, 43, 461-69 (1985)) which has the desired segment of T4 DNA in the same orientation as the $P_L$ sequence in p236, and also has a unique ClaI site within the regulatory region. This plasmid contains a deletion derivative (T4Δ) of the phage T4 protein 32 (gp 32) gene. T4Δ defines a deletion of the phage T4 protein 32 gene that fuses the promoter region followed by the first 7 amino-terminal codons (0.38 kb) to the last 8 carboxy-terminal codons followed by the transcription terminator (0.12 kb) through a BamH1 linker. We cleaved plasmid pTAK 21Δ with ClaI and filled in the site with DNA polymerase in the presence of dGTP and dCTP. We then cleaved with PstI and purified the longer resulting fragment.

In order to obtain $p_L$-pTAK 21Δ' (see FIG. 1A), we ligated the smaller of the two fragments obtained from the plasmid containing the $P_L$ sequence with the larger of the two fragments obtained from the plasmid containing the T4 sequence. This restored the PstI site and also connected the modified ClaI site to the modified R1 site to restore an EcoR1 site, but not a ClaI site. In addition to deletion T4Δ, $p_L$-pTAK 21Δ' has a further deletion between the EcoRI and ClaI sites of pTAK21A which removes the T4 promoter previously recognized by Krisch and Allet (*Proc. Natl. Acad. Sci. USA*, 79, 4937–41 (1982)).

We prepared plasmid $p_L$-pTAK 21Δ'-Cla+ (see FIG. 1A) from the plasmid $p_L$-pTAK 21Δ' by site specific mutagenesis using the gapped molecule technique (see B. A. Oostrea et al., *Nature*, 304, 456–59 (1983)) wherein the sequence 5'-AAAAAG-GAAATAAAAATGTTT AAA was replaced by 5'-AAAAAGGAAATCGATATGTTTAAA present in $p_L$-pTAK 21Δ'. This introduced a ClaI site between the Shine-Dalgarno (SD) sequence and the ATG initiating codon of the T4 regulatory region.

EXAMPLE 2

Preparation of Plasmid pAT153-pLT4 HTNF-(Gn) tet+

In order to prepare the plasmid pAT153-pLT4 HTNF(Gn) tet+, we began with the plasmid pBR322-Trp-IFN-Y-(Gn) (see European Patent Application Number 85902003.4, Publication Number 0174999) which has a DNA sequence between HindIII and BamH1 as follows: 5'-AAGCTTGCACCCAA(G)$_{16}$A(G)$_7$ ATCC (this G rich sequence is herein referred to as (Gn)). The sequences between BamH1 and PstI (clockwise) are from pBR322; the number (375) identifies the BamH1 site of pBR322 (see FIG. 1B). We found that destroying the ClaI or HindIII site of pBR322 (by filling in the site with Klenow) did not affect the Tet ® phenotype.

We cleaved plasmid pBR322-Trp-IFN-γ-(Gn) with restriction endonucleases HindIII and PstI. To the isolated fragment (shown in FIG. 1B as the DNA fragment clockwise between HindIII and PstI in plasmid pBR322-Trp-IFN-Y-(Gn)) we ligated the following three other fragments to produce plasmid pBR322 pLT4-HTNF-(Gn) (see FIG. 2): (a) the 1280bp PstI-ClaI fragment isolated from plasmid $p_L$-PTAK 21A-CLA+ (see FIG. 1A) by restriction digestion with PstI and ClaI; (b) a synthetic oligonucleotide linker containing one of the sequences in Table 1 and having ClaI and AvaI ends: and (c) a DNA fragment (see FIG. 1B iii HTNF CDNA (AvaI-HindIII)) containing the HTNF gene. The synthetic linkers used in the four-way ligation mixtures are shown in Table 1.

The nucleotide sequence of the HTNF cDNA clone has been published (see Marmenout et al., *Eur. J. Biochem.*, 152, 515–22 (1985); D. Pennica et al., *Nature* (London), 312, 724–29 (1984): T. Shirai et al., *Nature* (London), 313, 803–06 (1985): A. M. Wang et al., *Science*, 228, 149–54 (1985)). A unique AvaI site is situated within the first seven amino acids of the mature protein. A single HindIII site is located 125 bp downstream from the translation termination signal. We isolated the latter fragment from a plasmid containing the cloned HTNF cDNA gene (see Marmenout et al., *Eur. J. Biochem.*, 152, 515 (1985) and International Application Number PCT/EP85/00721, International Publication Number W086/03751) by restriction endonuclease digestion with AvaI and HindIII. We used one of several synthetic oligonucleotide linkers as shown in Table 1, to restore the seven N-terminal amino acids of the AvaI-HindIII fragment of the HTNF sequence as well as to insert that fragment into the pLT4 vector.

We synthesized these oligonucleotides on the Applied Biosystems 380A automated synthesizer. After standard deprotection, we desalted the crude oligonucleotides by C-28 SEP-PAK (Waters/Millipore Inc.), then purified on a preparative 7M urea/15% polyacrylamide gels (see T. Maniatis et al., *Biochemistry*, 14, 3787–94 (1975)). Each specific gene construction is designated by the oligonucleotide linker used for its synthesis. In this series, CA1, CA3, CA5 and CA13 all specify the natural HTNF amino acid sequence, but with different codon usages. Δ2 directs synthesis of a protein missing the first two amino acids and CA-his introduces a histidine residue, instead of arginine, as second amino acid of the mature protein. This is effected by a single base-pair mutation arising from the cloning of the CA1 linker.

In order to produce pAT153-pLT4 HTNF-(Gn) tet+, we cut plasmid pAT153 (see A. Twigg et al., *Nature*, 283, 216–18 (1980)) with EcoRI, filled in with dTTP, dATO and DNA polymerase, then cut with PstI. We then purified the longer of the two fragments. We next cut plasmid pBR322-pLT4-HTNF-(Gn) (produced by the four-way ligation described above) with BamHI, filled in with the four dXTPS and DNA polymerase, and then cut with PstI. We ligated this fragment to the EcoRI(filled)-PstI fragment of pAT153 to give pAT153-pLT4 HTNF-(Gn)tet+, a tetracycline-resistant plasmid that produces human tumor necrosis factor.

EXAMPLE 3

Preparation of T4 Ter Derivatives

In order to prepare a plasmid Containing the T4 gene 32 transcription terminator (T4-ter or ter plasmids), we prepared plasmid pAT153-pLT4 HTNF (Gn)-Sal (see FIG. 1C), cut this plasmid and ligated the resulting fragment of approximately 1100bp to a fragment of pasmid pAT153 and also to a synthetic oligonucleotide linker comprising the T4-ter sequence (see Table 1 and Krisch, H. M. and Allet, B., *Proc. Natl. Acad. Sci. USA*, 79, 4937–41 (1982)). This three-way ligation resulted in plasmid pAT53-pLT4 HTNF-T4-Ter.

We prepared plasmid pAT153-pLT4 HTNF(Gn)-Sal by introducing a SalI site immediately following the TGA translation termination codon of pAT153-pLT4 HTNF (Gn). (Introduction of the SalI site may be accomplished by any method of site specific mutagenisis, for example, the gapped molecule technique (see B. A. Oostrea et al., *Nature*, 304, 456–59 (1983)). As a result, the HTNF sequences 5'-TGAGGAGGACGAACAT were replaced by 5'-TGAGTCGACGAACAT.

We then cut plasmid pAT153-pLT4 HTNF (Gn) - Sal with the restriction endonuclease SaI and filled in the site with Klenow. We then cut with PstI. We isolated the resulting fragment of approximately 1100bp by agarose gel electrophoresis. In parallel, we cut plasmid pAT153 with EcoRI, then PstI, and isolated the larger fragment by agarose gel electrophoresis.

We next prepared a synthetic oligonucleotide linker comprising the T4 gene 32 transcription terminator sequence (see Krisch, H. M. and Allet, B., *Proc. Natl.*

*Acad. Sci USA*, 79, 4937-41 (1982)) and having an EcoRI site at one end and a Klenow treated HindIII site at the other end (see Table 1). We synthesized this oligonucleotide linker on the Applied Biosystems 380A automated synthesizer. After standard deprotection, we desalted the crude oligonucleotides by C-28 SEP-PAK (Walters/Millipore Inc.). We then purified the oligonucleotides on a preparative 7M urea/15% polyacrylamide gel (see T. Maniatis et al., *Biochemistry*, 14, 3787-94 (1975)).

We ligated the PstI- SalI fragment of pAT153-pLT4 HTNF (Gn)-SalI, the EcoRI-PstI fragment of pAT153 and the EcoRI-HindIII synthetic oligonucleotide linker which contained the ter sequence, to produce plasmid pAT153-pLT4-HTNF-T4-ter.

EXAMPLE 4

Preparation of Δ-pL Derivatives

In order to study the effects of using the T4 derived DNA segment alone, we removed the lambda $P_L$ derived segment between the PstI site (pBR322 map position 3607) or the DraI site (pBR322 map position 3232) and the EcoRI site at the junction between the $P_L$ and T4 derived DNA sequences (see FIG. 1B).

For example, to remove the lambda $P_L$ derived segment of plasmid pAT153-pLT4-HTNF-(Gn) (see FIG. 1B) in order to produce plasmid pAT153-T4-HTNF-(Gn) (see FIG. 1C), we first cleaved plasmid pAT153-pLT4-HTNF-(Gn), which confers resistance to both ampicillin and tetracycline antibiotics, by a mixture of EcoRI and PstI (or DraI) restriction enzymes, yielding a mixture of two fragments which we treated with the Klenow fragment in the presence of dATP and dTTP. We next separated the DNA fragments by agarose gel electrophoresis, then purified, self ligated and propagated the larger fragment of approximately 3600bp (EcoRI-PstI) or 3200bp (EcoRI-DraI) in *E.coli* W3110 (see Bachmann B. J., *Bacter. Rev.*, 36, 525 (1972)), thus generating the plasmids depicted in FIG. 1C as pAT153-T4-HTNF-(Gn).

This manipulation, which removes the lambda $P_L$ DNA sequences, also deletes part of the beta-lac-tamase gene (ampicillin resistance gene). The resulting plasmid is therefore ampicillin sensitive and tetracycline resistant.

EXAMPLE 5

Preparation of Plasmid pAT153 pLT4 HTNF CA3 cts T4 (ter or Gn)

In order to prepare a plasmid containing both the thermo-inducible repressor gene from bacteriophage lambda (cts gene) and the temperature-controlled $P_L$ promoter, it was necessary to isolate the approximately 1100bp fragment containing the cts gene from bacteriophage lambda DNA from strain cI857ind S7 (New England Biolabs, catalog #301-1, lambda DNA). To isolate this 100bp fragment, we cut lambda DNA with restriction endonuclease BglII, filed in with the four dNTPs and DNA polymerase, and then cut with PstI.

We then prepared a plasmid derivative of pAT153-pLT4-HTNF-(Gn) tet+by inserting a 270bp PstI-EcoRI DNA fragment containing the $P_L$ promoter into pAT153-pLT4-HTNF-(Gn), replacing the 1150bp PstI-EcoRI fragment which contains the beta-lactamase promoter, amino terminal half of the beta-lactamase gene and the original $P_L$ promoter, thus producing a pasmid that is ampicillin sensitive: plasmid pAT153-pLT4-HTNF-(Gn) tet+amp-. We then cut this plasmid with PstI and DraI, and isolated and ligated the larger fragment to the 1100bp BglII(filled)-PstI fragment containing the cts gene. This ligation produced plasmid pAT153-pLT4-HTNF cts (Gn). Derivatives in which (Gn) is replaced with T4 ter may be prepared in a manner as described in Example 3 to produce plasmid pAT153-pLT4-HTNF cts T4-ter (see FIG. 2).

EXAMPLE 6

Determination of the Structure of the T4 Promoter

In order to determine the structure of the T4 promoter, we isolated RNA samples from cells harboring the following Ter plasmids: pLT4-CA5, T4-CA5(Dra), pLT4-CA3, T4-CA3(Dra) and T4-CA5(Pst). We then identified transcription initiation sites and transcript sizes by S1 mapping and by Northern blot analysis.

Isolation Of RNA

We used the hot phenol extraction procedure of J. H. Miler (Experiments in Molecular Genetics (Cold Spring Harbor Laboratory, Cold Spring Harbor, New York) (1972)) to isolate RNA samples. After treating all buffers with 0.1% by volume of diethylpyrocarbonate (DEP), we heated the buffers for 10 min. at 80°.

We grew cells containing the T4 plasmids at 37° in complex medium (10 m) to an $OD_{575}$ of 1.0. We then added DEP (0.1% volume) and collected the cells by centrifugation.

We grew other cells containing the pLT4 plasmids at 30° in the complex medium (20 ml). At an $OD_{575}$ of approximately 0.6, we transferred a 10 ml aliquot of the pLT4 plasmid-harboring cells to 42°, then allowed the two cultures (30° and 42°) to grow for an additional hour. We then added DEP (0.1% volume) and collected these cells by centrifugation.

After centrifugation, we resuspended the pellets of each mixture of cells in 2 ml of 20 mM Na-acetate pH 5.5, 1 mM Na-EDTA and 0.5% SDS at 60°. We then added pre-heated phenol (2 ml) saturated in the same Na-acetate pH 5.5 buffer, vortexed the mixtures vigorously for 15 sec., incubated for 30 sec. at 60° and vortexed again for 30 sec. After centrifuging again (5 min., 4°), we collected the upper aqueous phases and repeated the phenol treatment described above.

We then added 0.2 ml of 3M Na-acetate, 10 mM Na-EDTA and 6.5 ml ethanol to the aqueous phases, incubated the mixtures for 10 min. at 70° and centrifuged for 20 min. at 15000 rpm (4°). We dried the pellets from each mixture in vacuo, redissolved the pellets in 0.3 ml of 0.3 M Na-acetate, 1 mM Mg-acetate, 1 mM Na-EDTA, and then transferred the mixtures to Eppendorf tubes and ethanol precipitated. We then washed the precipitates once in 80% ethanol, dried the precipitates, then redissolved in 100 μl of distilled water.

S1 Mapping

We designed an S1 mapping experiment to pinpoint transcription initiation site(s) within the $P_L$ and T4 DNA sequences.

We first mixed 5 μl of RNA, isolated as above, with 45 μl of 0.3 M Na-actate, 1 mM EDTA. We then ethanol precipitated the mixture, washed once in 80% ethanol, dried the precipitate, then resuspended the precipitate in 20 μl of 40 mM Pipes pH 6.4, 0.4 M NaCl, 1 mM Na-EDTA. In parallel, we cleaved pLT4-HTNF-cts plasmid DNA (FIG. 2) by ClaI and labelled the sites at the 5' end with γ-$^{32}$P-ATP using T4-polynucleotide kinase. After cleavage with PatI, we used as 5% polyacrylamide gel to isolate the fragment of 405 bp that contains the $P_L$ and T4 DNA sequences. We next dissolved the isolated fragments in water (50 μl), heated the mixtures to 95° for 2 min. to separate the strands, then chilled the resulting mixture quickly. We next added 2 μaliquots of the 5'-labelled DNA to the RNA samples, isolated as above in Pipes buffer, then incubated the RNA and DNA mixtures at 65° to 90 min.

We then added S1 buffer (200 μl of 0.03M Na-acetate pH 4.6, 0.25 M NaCl, 1 mM ZnSO$_4$) and 2,000 units of S1 nuclease to the mixtures. We incubated the reaction mixtures for 30 min. at 37°, then ethanol precipitated the samples, washed the precipitate in ethanol, and finally dissolved the precipitate in sample buffer for sequencing in denaturing polyacrylamide gel (see A. M. Maxam and W. Gilbert, *Proc. Natl. Acad. Sci. USA*, 74, 560–64 (1977)). As size markers, we included in the same sequencing gel a series of partials obtained by sequencing the fragment of 405bp labelled at the ClaI site.

Figure 5A:
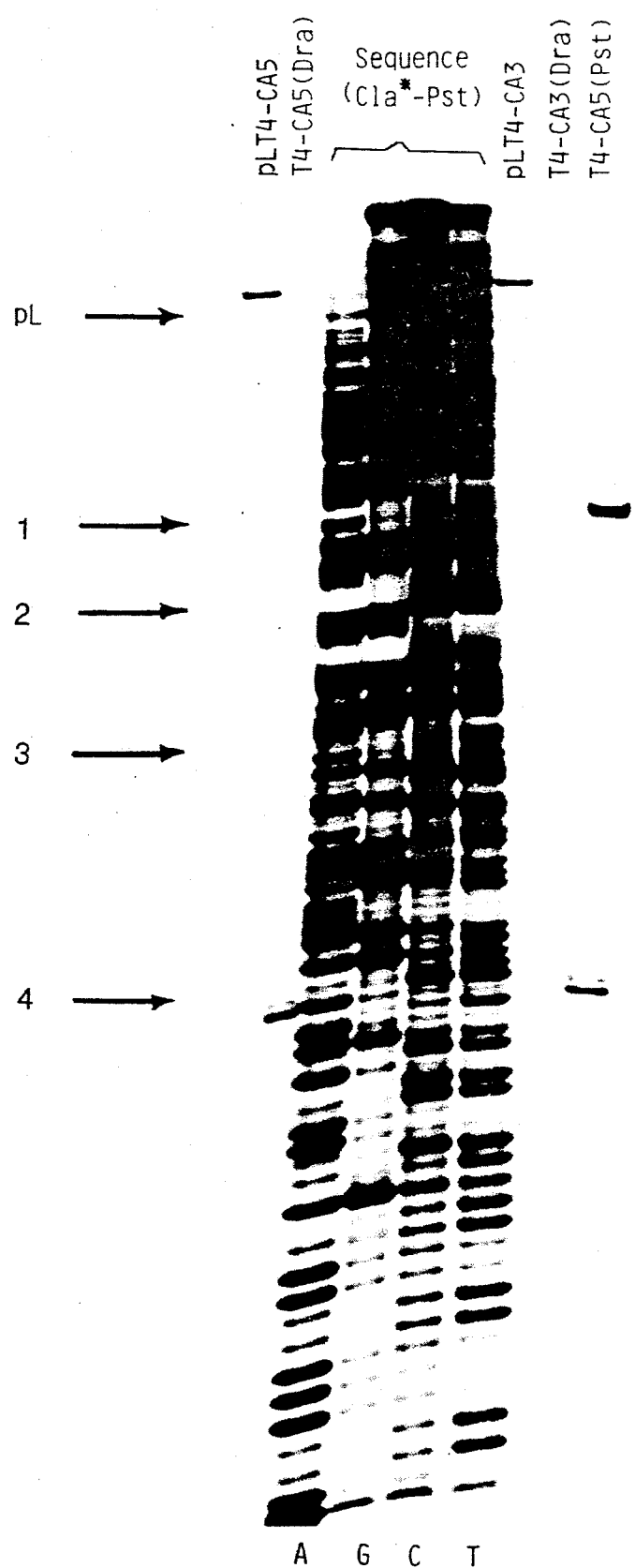
FIG. 5A and FIG. 5B depict a DNA sequence derived from bacteriophage T4 that acts as a promoter (hereinafter referred to as the T4 promoter). As shown in the figure, the T4 sequence may be fused to pBR322 sequences at either the PstI (3607) or DraI site (3232). Also shown in FIG. 5A are the results of S1 mapping experiments analyzed by polyacrylamide gel electrophoresis. The RNA samples were prepared from cells harboring pLT4-CA5, T4-CA5(Dra), pLT4-CA3, T4-CA3(Dra) and T4-CA5(Pst) plasmids. All of these plasmids had the T4 gene 32 transcription terminator (hereinafter referred to as T4-ter or Ter plasmids). In the figure, arrows point to an RNA polymerase binding site in the $P_L$ DNA sequence and four such sites in the T4 DNA sequence.
Figure 5B:
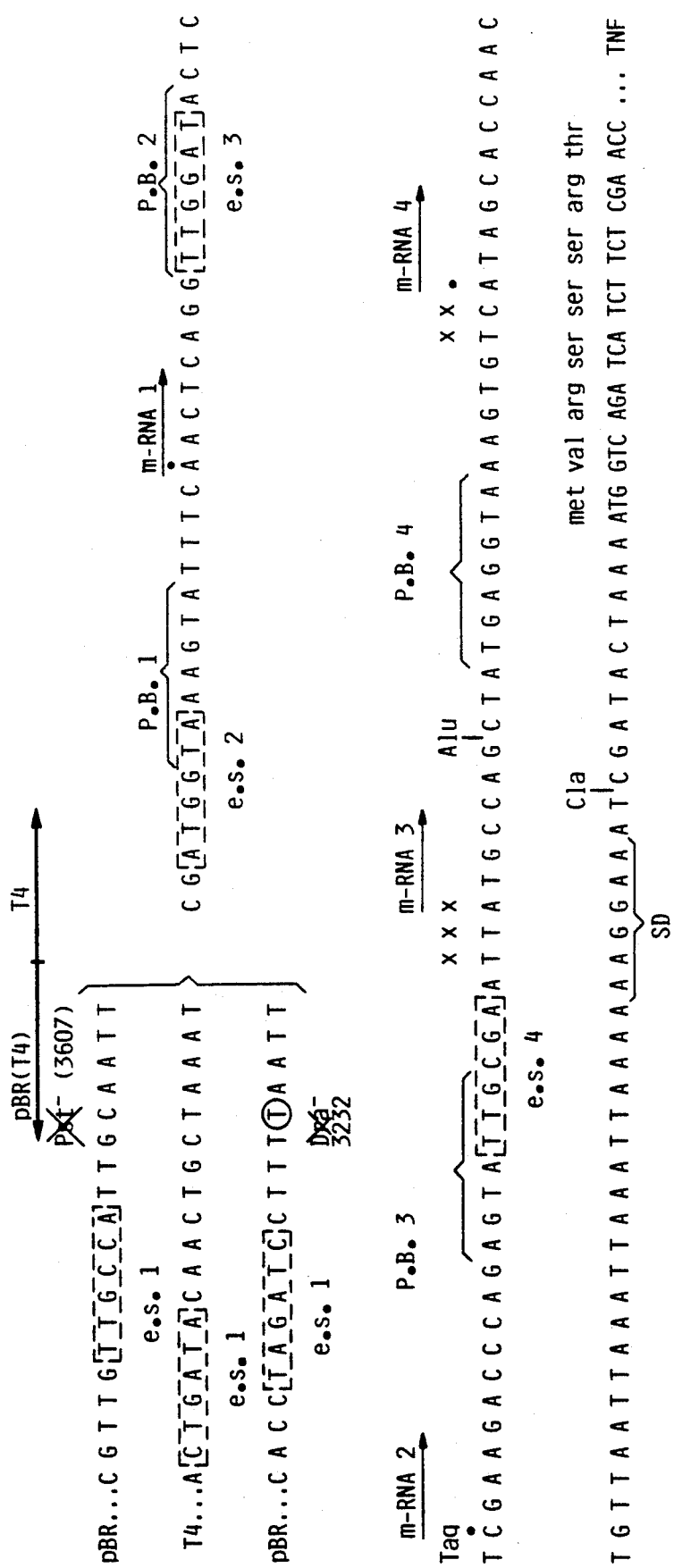

As shown in FIG. 5A, four mRNA starting sites (corresponding to four promoters, designated by circled numbers 1 through 4) were identified within the T4 DNA and one (as expected) within the $P_L$ DNA. Along the sequence drawn in the figure, the abbreviation P.B. is used to designate various "Pribnow Boxes". These Pribnow Boxes are strong RNA-polymerase binding sites. The abbreviation e.s. is used in the figure to designate entry sites for RNA-polymerase. The locations of these sites were inferred by analogy to the consensus structure of the *E.coli* promoters.

As seen in the autoradiogram of FIG. 5A, the four mRNA species, from plasmids comprising pLT4-CA5, T4-CA5(Dra), pLT4-CA3, T4-CA3(Dra) and T4-CA5(Pst) sequences, occur as bands of different intensities. The numbers 1 through 4 below designate each of the four RNA transcription units, each of a different length and initiating from a different RNA polymerase binding site in the T4 DNA sequence.

Interestingly, when the T4 fragment is fused to the DraI site of pBR322 (T4-Dra plasmid) the band corresponding to mRNA 4 is the most prominent. By contrast, mRNA 1 is predominant when the T4 fragment is connected to the PstI site of pBR322 (T4-Pst plasmid). This suggests that promoter 1 created by the PstI junction is stronger than that formed by the DraI junction, and also stronger than promoter 4. However, HTNF protein expression levels from plasmids comprising T4-Dra and T4-Pst sequences are indistinguishable (not shown). Moreover, the pLT4 derivatives (CA3 and CA5) only exhibit the mRNA species starting at the $P_L$ promoter, as if virtually no mRNA transcripts were initiating from the T4 promoter(s) in the presence of $P_L$. Results of Northern blot analyses (described below), which detected transcripts not seen by the S1 mapping, show that these interpretations are incorrect. Thus, the S1 mapping technique, while useful in identifying transcription initiation sites, is inadequate to quantitatively analyze transcripts arising from multiple promoters.

Northern Blot Analysis

We performed a Northern blot analysis in order to determine more specifically the number of discrete RNA species initiating from the T4 promoter sequence and thus confirm the assumed multiple promoter structure of the T4 sequence. To perform the Northern blot analysis we first denatured RNA samples, isolated as above, by treating the samples for 15 min. at 60° in loading buffer (50% formamide, 2.2 M formaldehyde, 20 mM borate pH 8.4, 1 mM EDTA, 0.05% bromophenol blue). We loaded the denatured samples onto horizontal 1.2% agarose - 2.2 M formaldehyde gels buffered in 20 mM borate pH 8.4, 1 mM EDTA, then electrophoresed at 80 V for 5 hours. After soaking in TAE buffer (40 mM Trisacetate pH 7.4, 1 mM Na-EDTA), we electroblotted the gels onto Gene Screen Plus (New England Nuclear) membrane filters according to the manufacturer's recommendations.

We prepared $^{32}$P-labelled probes from the 610bp ClaI-HindIII fragment (FIG. 2, (Gn) plasmid) containing the HTNF gene (TNF specific probe) and from the 280 bp PstI-EcoRI fragment ($P_L$ promoter probe) by nick translation. We then prehybridized the RNA on the membrane filters for 2 hours at 42° (6xSSC, 50% formamide, 5×Denhart's solution, 0.1% SDS and 250 μg/ml sonicated salmon sperm DNA). We then hybridized the RNA with the labelled probes for 18 hours at 42° (prehybridization buffer plus 250,000–500,000 cpm/ml probe). Finally, we rinsed the membrane filters in 2xSSC, washed for 20-30 min. at 55° in 0.2×SSC, and then exposed the filters to X-ray films.

Using the nick translated probe comprising only $P_L$ DNA sequences, we did not detect, as expected, any transcript in the T4 RNA samples. The pLT4 RNA samples exhibited a discrete RNA species of 760 bases, which corresponds, presumably, to a transcript starting at the $P_L$ promoter, extending trough the HTNF gene and terminating at Ter. The pLT4 RNA sample from the induced culture (42°) shows a strong signal which is weakly visible in the non-induced culture (30°). With the probe that comprises only HTNF coding sequences, all the T4 and pLT4 samples exhibit a discrete band of 540 bases corresponding to mRNA molecules that start within the T4 sequences at mRNA 4, extend into the HTNF gene and terminate at Ter. In addition, the pLT4 sample (42°) exhibits the $P_L$ transcript of 760 bases; and the T4-Pst sample superimposes a species slightly larger than 540 bases consisting, presumably, of a transcript initiated at mRNA 1.

These interpretations are confirmed by FIG. 6B where homologous plasmids (CA3) with Ter or (Gn) are compared. The (Gn) plasmids (which lack an authentic terminator) fail to generate the discrete mRNA species. Instead, the Northern blot analysis detects more diffuse bands of larger molecular weights especially for the pLT4 sample. In the T4-(Gn) sample, a significant amount of HTNF RNA material accumulates in a region that would be consistent with a transcript started at the T4 promoter and terminated near the (Gn) tail (note that the (Gn) tail is 125 bp downstream from the TGA stop codon, whereas Ter is adjacent to this codon).

It is striking that the Northern blot analysis detects two transcripts that are not seen by S1 mapping, i.e., the T4 transcript in pLT4 RNA samples and the mRNA 4 transcript in RNA from T4-Pst plasmids. Because S1 mapping was conducted with total non-fractionated RNA, heterogeneously-sized mRNA molecules generated by the multiple transcription initiation sites were present in the mixture with the discrete DNA probe. RNA molecules having long stretches of homology with the DNA probe could displace molecules with shorter homology during the hybridizations, especially as RNA was in excess over DNA. By this mechanism, RNA transcripts initiated further upstream at the $P_L$ promoter would be over-represented in the S1 mapping experiments relative to transcripts initiated downstream at the T4 promoters. Such a bias was obviously eliminated in the Northern blot analysis which detected electrophoretically separated RNA molecules, thus identifying the various RNA species more reliably. Moreover, T4-CA3 and T4-CA5 transcripts are equally abundant even though HTNF protein obtained from CA3 is significantly lower than from CA5, as shown later. This indicates that translation, rather than transcription, is limiting expression from CA3.

EXAMPLE 8

Determination of Effect of Multiple Promoter Structure

Figure 7A:
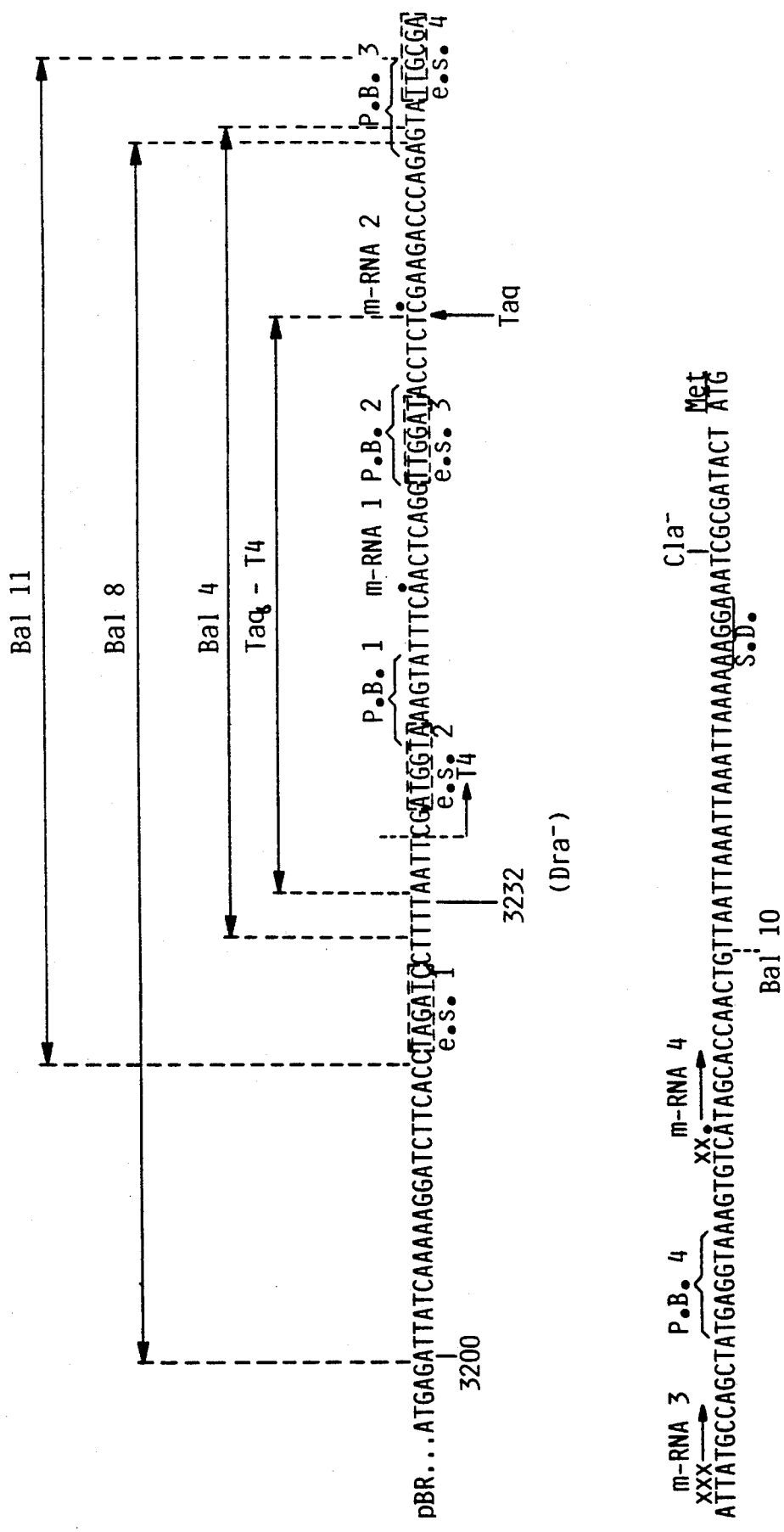
FIG. 7A and FIG. 7B show a deletion map of the T4 promoter wherein the DNA sequences of Taq-T4, Bal4, Bal8, Bal11 and a partial DNA sequence of BA110, are identified.

To test the effect of the multiple, as opposed to a unique, promoter structure on gene expression we prepared Bal31 nuclease deletion derivatives of T4-Δ2-Ter (FIG. 7A and 7B) and compared their ability to promote protein synthesis with the original plasmid.

We derived Taq-T4 from T4-Δ2, then derived Bal., 8, 10 and 11 from Taq-T4. After filling in the ClaI site of T4-Δ2 between SD and the initiating ATG with Klenow to avoid cleavage by Taq1, we removed the T4 sequences upstream from the unique Taq1 site in the T4 DNA. We then fused the end points of the Taq-T4 deletion through an AsuII site (created by a DraI-Taq-K junction). We derived Bal4, 8, 10 and 11 from Taq-T4 by nibbling from the unique AsuII site with Bal31, adding XbaI linkers (5'-CTCTAGAG) followed by XbaI cleavage, and religating the linear molecules.

We determined the DNA sequences of the resulting derivatives by the method of Maxam and Gilbert (*Proc. Natl. Acad. Sci. USA*, 74, 560–64 (1977)). Taq-T4, Bal4 and Bal8 all have intact promoter 4 (e.s. 4, P.B. 4 and mRNA 4) (FIG. 7A), but elements of the other three promoters have been deleted. The right end point of the Bal11 deletion lies within e.s. 4, which is therefore inactivated. Bal10 has the ribosome binding site, but the complete T4 promoter has been deleted.

Figure 7B:
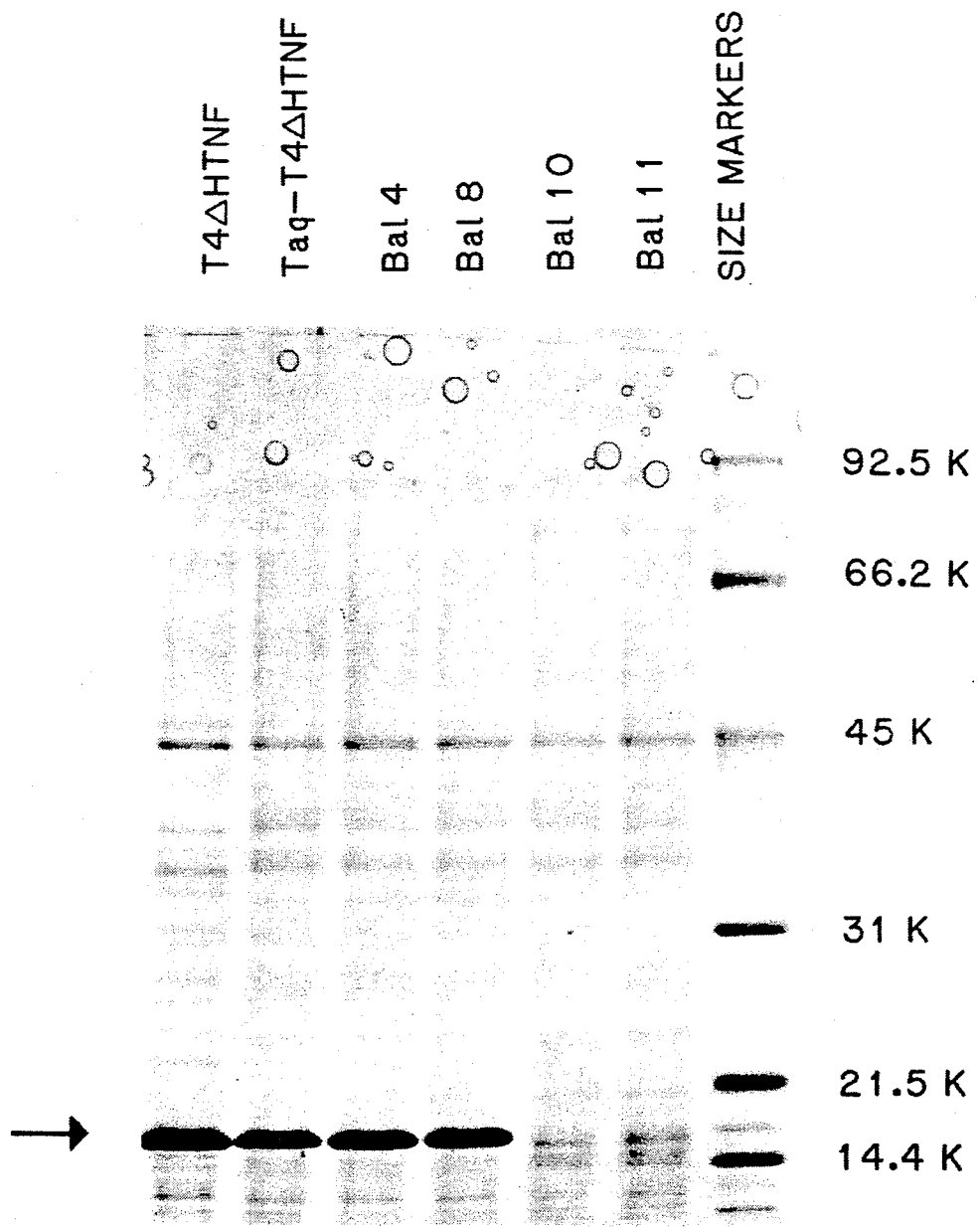

Analysis by densitometry tracing of the gel shown in FIG. 7B indicates that the original plasmid expresses 53% of the total *E.coli* protein mass as HTNF, whereas protein levels of 38–41% are measured with the Bal4 and Bal8 derivatives in which the three promoters are missing. Bal10 and 11 fail to express detectable levels of HTNF. The results of the S1 mapping and Northern blot analyses, together with the deletion analysis, are consistent with the assignment of several efficient promoters within the T4 DNA fragment. Moreover, the deletion analysis shows that the structure of tandem promoters contributes to the overexpression of a desired protein.

EXAMPLE 8

Determination of Effect of Different Synthetic Oligonucleotide Linkers on Levels of Protein Expression In order to analyze protein expression from HTNF variants, we first propagated T4-CA1, T4-CA-his, T4-CA3, T4-CA5, T4-CA13, T4-Δ2, pLT4-CA1, pLT4-CA-his and pLT4-CA13 plasmids in a λ+*E.coli* c600 derivative: thr-1, leuB6, thi-1, supE44, laoY1, tonA21, hsr−, hsm+. For plasmid preparations, we grew the *E.coli* c600 transformants at 37° in LB broth (1% bactotryptone, 0.5% bacto yeast extract, 0.5% NaCl, pH adjusted to 7.0 with NaOH) supplemented with ampicillin (40 μg/ml) or tetracycline (5 μq/ml).

After selecting plasmids, propagated as above, for HTNF protein expression, we then transformed (see T. Maniatis et al., Molecular Cloning, a Laboratory Manual (Cold Spring Harbor Laboratory, Cold Spring Harbor, New York) (1982)) W3110, an *E.coli* K12 (λ−, F−) prototroph (see B. J. Bachmann, *Bact. Rev.*, 36, 525–57 (1972)). We grew the transformants in complex medium containing casamino acids, yeast extract, gycerol, and the appropriate antibiotic (ampicillin (40 μg/ml) or tetracycline (5 μg/ml)) within shake flasks under vigorous agitation (240 rev. per minute on a G10 Gyrotory Shaker, New Brunswick Scientific). We grew *E.coli* W3110 transformants carrying plasmids containing the non-inducibe T4 promoter (T4-CA1, CA-his, CA3, CA5, CA13 or Δ2 pasmids) overnight at 37° C. to an $OD_{575}$ between 6 and 10. When we incorporated the heat-inducible cts gene into a pLT4 plasmid, we grew the cells at 30°. For heat induction experiments, designed to determined whether additional protein expression could be achieved by activating the $P_L$ promoter in pLT4 transcripts, we grew aliquots of the culture at 30° to an $OD_{575}$ of 2.0, then transferred an aliquot to 42° and allowed growth of the two samples (30° and 42°) to continue for at least 2 hours.

We then prepared protein samples (approximately $2 \times 10^2$ $OD_{575}$ equivalents) from the cultured cells for analysis by gradient SDS-polyacrylamide gel electrophoresis. In order to perform the gradient SDS-polyacrylamide gel electrophoresis, we first centrifuged (in Eppendorf tubes) cells grown in the complex medium (1 ml), resuspended the cells in 500 μl of sample buffer (50 mM Hepes pH 8, 30 mM NaCl, 4% SDS, 4M urea, 1% β-mercaptoethanol, 0.05% bromophenol blue), heated the mixture to 95° C. for 10 min., then centrifuged the mixture for 10 min. at 15,000 rpm. We loaded aliquots of the supernatant (2–4 μl, corresponding to $10^{-2}-10^{-1}$ $OD_{575}$ equivalents) in gradient (10–20%) SDS-polyacrylamide gels (see U. K. Laemmli, *Nature*, 227, 680–85 (1970)), and then stained with Coomassie Brilliant Blue.

Surprisingly, the results of the electrophoresis analysis showed that plasmids constructed with the oligonucleotide linkers CA-his, CA5 or Δ2 (Table 1) expressed high levels of HTNF protein as pLT4 constructs under conditions of temperature (30°) that do not induce transcription from the heat-inducible $P_L$ promoter. This high level expression was fully retained when the $P_L$ sequences were deleted to generate the corresponding T4 constructs (see FIGS. 1B and 1C). In contrast, the results of the electrophoresis analysis show that plasmids containing the CA1, CA3 or CA13 linkers (Table 1) expressed little HTNF when the $P_L$ sequences were deleted to generate the corresponding T4 constructs; these plasmids also expressed little HTNF as pLT4 constructs under conditions of temperature (30°) that do not induce transcription from the heat-inducible $P_L$ promotor.

Figure 8:
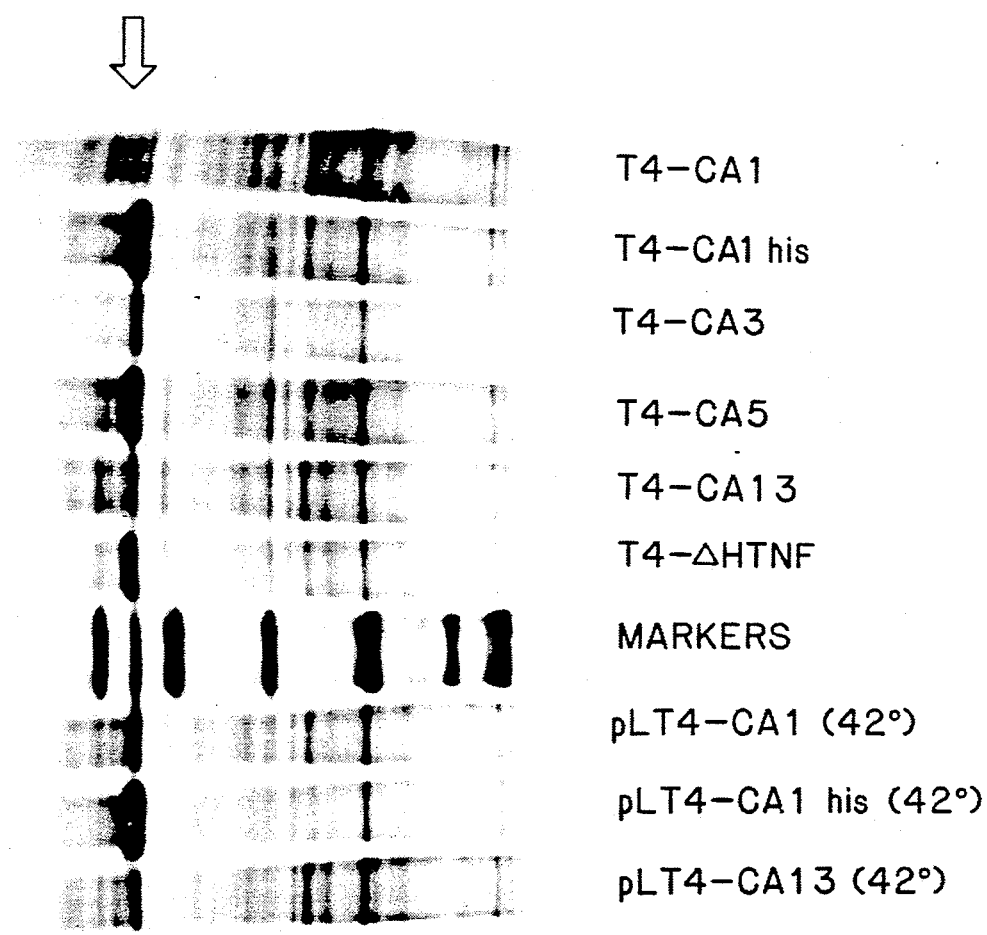
FIG. 8 depicts the results of SDS-polyacrylamide gel electrophoresis of protein expression levels from HTNF variants. All of the plasmids used have the T4 terminator. The arrow points to the HTNF band of 17.5K-daltons.

Typical results of the SDS-polyacrylamide gel electrophoresis are depicted in FIG. 8. All the plasmids referred to in the figure have the T4 terminator. The arrow points to the HTNF band of 17.5K-daltons. The marker proteins are the SDS-PAGE low molecular weight standards (catalog #161-0304, Bio-Rad Laboratories, Richmond, CA) as in FIG. 7B.

T4-CA1 and T4-CA-his differ ony by one base (see Table 1) in the early part of the gene. This mutation replaces an arginine by a histidine residue in the protein. As shown by SDS-polyacrylamide gel electrophoresis in FIG. 8, this unique change substantially affects the protein expression level of the gene.

The figure also shows that pasmids T4-CA3 and T4-CA5 have different expression levels. These plasmids encode the same HTNF polypeptide, but have three alterations in the codon usage near the aminoterminal end (Table 1). Such alterations are possible because of redundancies in the DNA code which allow one skilled in the are to pick and choose among certain nucleotides without changing the amino acid that the sequence codes for. T4-CA5, in addition, has three A residues preceding the ATG initiating codon. These residues are probably not essential for high level expression, because they are deleted in T4-CA-his and T4-Δ2 genes which are, nevertheless, highly expressed (FIG. 8).

FIG. 8 also shows the protein patterns obtained with the pLT4 derivatives of CA1, CA-his and CA13 after heat inactivation of the cts repressor gene. An active $P_L$ promoter enhances expression from pLT4-CA1 and (to a lesser extent) pLT4-CA13, but not from pLT4-CA-his. Similar results (not shown) are observed with pLT4-CA3 (enhancement) and pLT4-CA5 (no enhancement of expression from the $P_L$ promoter). Efficient translation of the constitutive T4 transcripts made from plasmids containing pLT4-CA-his and pLT4-CA5 has probably saturated the cells' ability to accumulate more HTNF protein before $P_L$ induction, thus masking the additional contribution of the $P_L$ transcript in protein synthesis.

In DNA reconstruction experiments (designed to control random mutation by a procedure involving the reassembling of fragments of plasmids which are known to be free of mutation), in which the pairs of AvaI or ClaI fragments of the various plasmids were exchanged, we confirmed that the DNA sequences within the synthetic linkers (Table 1) were solely responsible for the differential expression levels seen in FIG. 8.

These results indicate that minor differences in the DNA sequences of linkers have substantial consequences on the level of expression of a desired protein. While we do not wish to be bound by any theory, we believe that changing the DNA sequence of the synthetic oligonucleotide linker most probably affects protein expression at the translation level by a mechanism involving mRNA secondary structure, i.e., base pairing of homologous sequences on the mRNA.

EXAMPLE 9

Effect of T4 Gene 32 Transcription Terminator on Level of Protein Expression

To analyze the effect of the T4 gene 32 transcription terminator on the level of expression of a desired protein, we compared (Gn) and Ter containing plasmids for HTNF production levels. These plasmids had either a 24$^{mer}$ poly-G tail 3' to the HindIII site ((Gn) plasmids) or a synthetic T4 terminator sequence (see Table 1) introduced just after the HTNF translation termination signal, thus deleting the 125 bp of 3'-untranslated DNA (Ter plasmids). By densitometry tracing measurements of polyacryamide gels, we found that the Ter plasmid constructions expressed consistently more HTNF protein than the corresponding (Gn) plasmid constructions.

Figure 9:
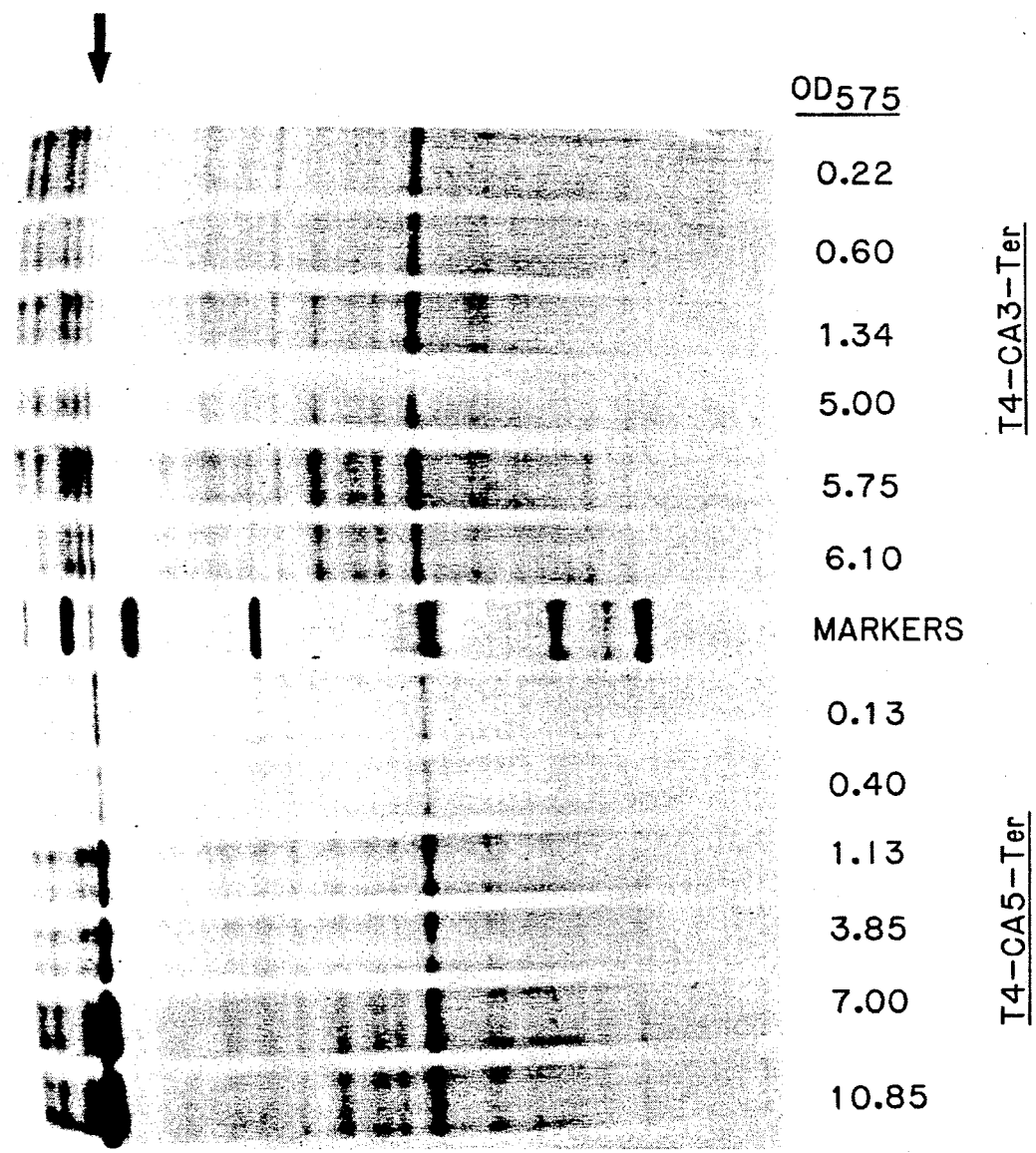
FIG. 9 depicts the results of gradient SDS-polyacrylamide gel electrophoresis of HTNF expression during cell growth of E.coli W3110 cells containing T4-CA3-Ter and T4-CA5-Ter plasmids.

FIG. 9 shows the analysis of protein samples taken at various times during fermentation in complex medium of bacteria containing the T4-CA3-Ter or T4-CA5-Ter plasmids. During the exponential growth phase ($OD_{575}$ of about 1 to 5) the HTNF content relative to the total protein mass is lower than during the stationary phase ($OD_{575}$ higher than 5) by a factor of at least 2, as judged by densitometry tracing measurements. The same effect is observed when complex medium is replaced by LB broth or M9 medium. This effect is less pronounced with T4-CA5 in which Ter has been deleted or replaced by (Gn) (not shown).

Figure 10:
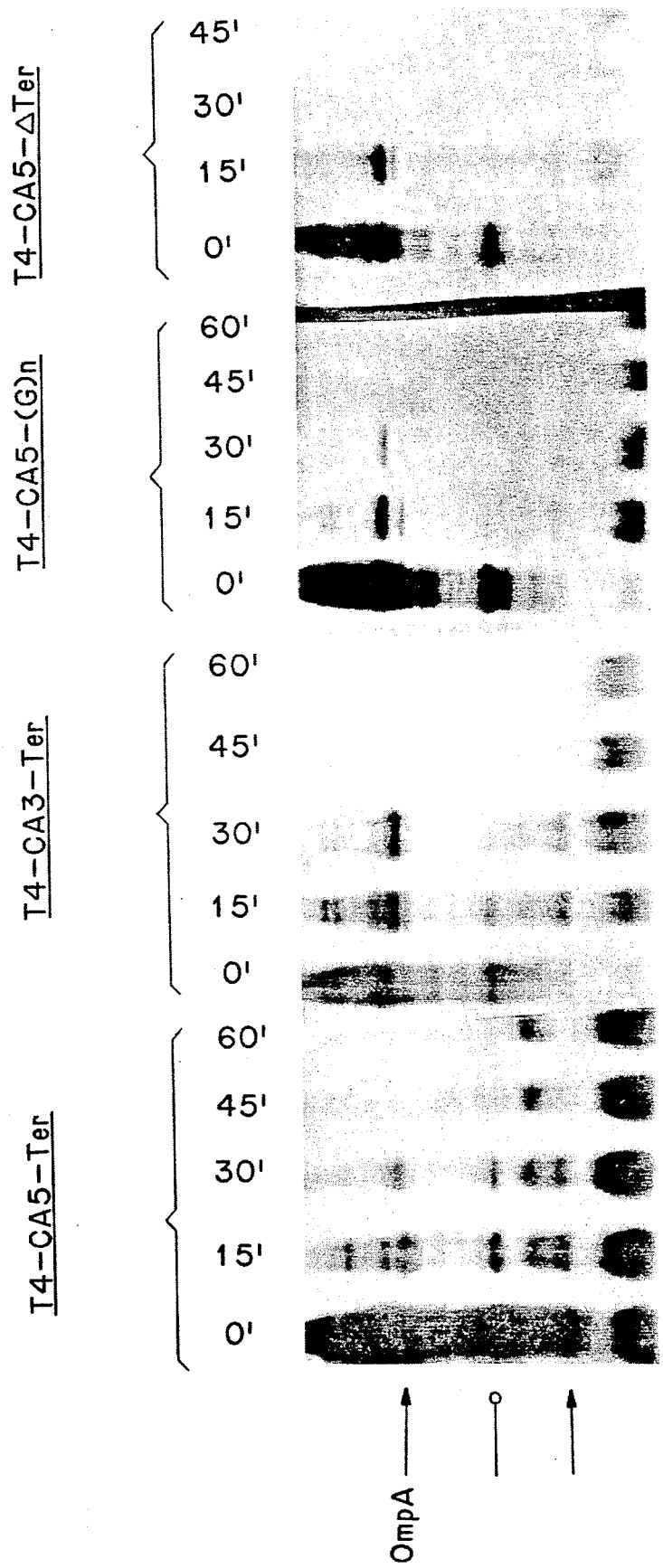
FIG. 10 depicts autoradiography of the results of SDS-polyacrylamide gel electrophoresis of protein synthesis of cultures of E.coli W3110 carrying T4-CA5-Ter, T4-CA3-Ter, T4-CA5-(Gn) and T4-CA5-ΔTer plasmids after arrest of RNA transcription by the addition of rifampicin. The upper arrow points to the stable 32K-dalton Ompa protein and the lower to the stable lipoprotein of 7.5K-daltons. The circled horizontal line shows the HTNF protein.

The reason for this unexpected difference became apparent in the mRNA stability studies shown in FIG. 10, which monitored the ability of exponentially growing cells to synthesize proteins at various times after transcription had been arrested by rifampicin addition. As will be discussed below, the T4 transcription terminator stabilizes the mRNA started at the T4 promoters and accounts for the two modes of expression observed for the Ter plasmids.

In order to evaluate the mRNA stability of T4 plasmids having different terminator sequences, we first grew cultures of *E.coli* W3110 carrying T4-CA5-Ter, T4-CA3-Ter, T4-CA5-(Gn) and T4-CA5-ΔTer. We obtained plasmid T4-CA5-ΔTer by deleting the T4 synthetic terminator present in T4-CA5-Ter (see FIG. 1C). We grew cells containing these HTNF plasmids at 37° in 25 ml of M9 medium supplemented with 0.2% casamino acids to an $OD_{575}$ of 0.5. we then centrifuged and resuspended in 20 ml of the same medium, except that the concentration of casamino acids was 10 times lower.

We next incubated the cells at 37° for 10 min. and transferred a 2.5 ml aliquot of the cultured cells into a separate tube for pulse-chase labelling. At the same time, we added rifampicin to the remainder of the culture (200 μg/ml final concentration). To perform the pulse-chase labelling for the 0 min. control we first added 5 μCi of $^{14}$C-amino acid mixture (Amersham) to the 2.5 ml aliquot and allowed cell growth to continue at 37° for 5 min. At that time, we added excess cold amino acids (0.2% final concentration) and allowed the chase to proceed for 5 min. We then centrifuged the cells and resuspended in 30 μl of SDS gel sample buffer. We took aliquots of the rifampicin-treated culture at 15 min., 30 min., 45 min. and 60 min. after the addition of rifampicin. We analyzed each aliquot by pulse-chase exactly as described above for the 0 min. control.

We next heated the radioactive protein samples at 95° for 10 min., centrifuged at 15,000 rpm for 10 min., and then electrophoresed in 12.5SDS-polyacrylamide gels. We then soaked the gels in an autoradiography enhancer solution (NEF-974, New England Nuclear), dried the gels and exposed them to X-ray films.

FIG. 10 depicts autoradiography of the results of SDS-polyacrylamide gel electrophoresis of protein samples taken at various times after arrest of RNA transcription. At zero time, i.e., the time of rifampicin addition, all the *E.coli* proteins, including HTNF, were synthesized. After arrest of transcription, ony proteins made from previously synthesized, stable mRNAs would be detected. Two *E.coli* proteins, the OmpA protein of 32K-daltons and a lipoprotein of 7.5K-daltons, are synthesized from stable mRNA (see A. Hirashima et al., *J. Mol. Bio.*, 79, 373-89 (1973)) and served as internal controls in the HTNF mRNA stability studies. As seen in the figure, T4-CA5-Ter and T4-CA3-Ter synthesized HTNF protein up until 30 min. after rifampicin addition, whereas T4-CA5-(Gn) and T4-CA5-ΔTer did not. In each case, the decay of HTNF production is comparable to the decay of the OmpA protein and the lipoprotein which have an mRNA half-life of more than 10 min. These results establish that the T4 terminator stabilizes the mRNA started at the T4 promoters.

Stability of mRNA accounts for the two modes of protein expression observed for T4-CA3-Ter and T4-CA5-Ter (FIG. 9). During the exponential growth phase, a pool of HTNF mRNA reflects an equilibrium between the rates of cell division and of stable mRNA synthesis. As the cell division rate is decreased (stationary phase), stable mRNA molecules presumably continue to be synthesized and accumulate in the cell. This mechanism allows the T4 promoters to establish very high levels of mRNA, and hence very high levels of protein production.

While we have hereinbefore described a number of embodiments of this invention, it is apparent that our basic constructions can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

We claim:

1. A method for improving the expression of a non-bacteriophage T4 protein comprising culturing a prokaryotic host transformed with a recombinant DNA molecular capable of directing expression of said non-bacteriophase T4 protein in high yields in said prokaryotic host, said recombinant DNA molecule comprising the following elements, operatively linked in the following order, 5' to 3': DNA sequence I, DNA sequence X, DNA sequence coding for anon-bacteriophage T4 protein, wherein said DNA sequence I consists of:

CGATGGTAAAGTATTTCAA
              CTCAGGTTGGATACCTCTCGAAG
ACCCAGAGTATTGCGAATTATGCCAGCTATG
              AGGTAAAGTGTCATAGCACCA
ACTGTTAATTAAATTAAATTAAAAAGGAAAT, said DNA sequence X comprises a DNA sequence selected from the group consisting of CGATACT, CGCGATACT, ATACTAAA, ATACT, OGCGATACTAAA, CGATACTAA and CGATTCC and said non-bacteriophase T4 protein is selected from the group consisting of human interleukin 2 and human tumor necrosis factor.

2. The method according to claim 1, said DNA molecular further comprising a non-bacteriophage T4 promoter, said recombinant DNA molecule comprising the following elements, operatively linked in the following order, 5' to 3'; non-bacteriophage T4 promoter, DNA sequence I, DNA sequence X, DNA sequence coding for a non-bacteriophage T4 protein.

3. The method according to claim 2, wherein said promoter is a P$_L$ promoter.

4. The method according to claim 1, said DNA molecular further comprising bacteriophage T4 transcription terminator sequence, said recombinant DNA molecule comprising the following elements, operatively linked in the following order, 5' to 3': DNA sequence I, DNA sequence X, DNA sequence coding for a non-bacteriophage T4 protein, bacteriophage T4 transcription terminator sequence.

5. The method according to claim 4, wherein said T4 transcription terminator sequence comprises the DNA sequence:

AGCTTGGGGACCCTAGAGGTCCCCTTTTTTATTTTG
TCGAACCCCTGGGATCTCCAGGGGAAAAAATAAAACTTAA.

6. The method of any one of claims 3, 5, 2, 4, and 1 wherein said host is not infected by bacteriophage T4.

7. A recombinant DNA molecule comprising the following elements, operatively linked in the following order, 5' to 3': DNA sequence I, DNA sequence X, DNA sequence coding for a non-bacteriophage T4 protein, wherein said DNA sequence I consists of:

CGATGGTAAAGTATTTCAA
              CTCAGGTTGGATACCTCTCGAAG
ACCCAGAGTATTGCGAATTATGCCAGCTATG
              AGGTAAAGTGTCATAGCACCA
ACTGTTAATTAAATTAAATTAAAAAGGAAAT, said DNA sequence X comprises a DNA sequence selected from the group consisting of CGATACT, CGCGATACT, ATACTAAA, ATACT, CGCGATACTAA, CGATACTAAA and CGATTCC and said non-bacteriophage T4 protein is selected from the group consisting of human interleukin 2 and human tumor necrosis factor, said recombinant DNA molecule directing expression of said non-bacteriophage T4 protein in high yields in a prokaryotic host.

8. The recombinant DNA molecule of claim 7, further comprising a non-bacteriophage T4 promoter, said recombinant DNA molecule comprising the following elements, operatively linked in the following order, 5' to 3': non-bacteriophage T4 promoter, DNA sequence I, DNA sequence X, DNA sequence coding for anon-bacteriophage T4 protein.

9. The recombinant DNA molecule of claim 8, wherein said promoter is a P$_L$ promoter.

10. The recombinant DNA molecule of claim 7, further comprising a bacteriophage T$_4$ transcription terminator sequence, said recombinant DNA molecule comprising the following elements, operatively linked in the following order, 5' to 3': DNA sequence I, DNA sequence X, DNA sequence coding for a non-bacteriophage T4 protein and a bacteriophage T$_4$ transcription terminator sequence.

11. The recombinant DNA molecule of claim 10, wherein said T4 transcription terminator sequence comprises the DNA sequence:

AGCTTGGGGACCCTAGAGGTCCCCTTTTTTATTTTG
TCGAACCCCTGGGATCTCCAGGGGAAAAAATAAAACTTAA.

12. A procaryotic host transformed with the recombinant DNA molecule of any one of claims 9, 11, 7, 8, and 10.

13. A prokaryotic host according to claim 12, wherein said host is not infected by bacteriophage T4.

* * * * *